US006248554B1

(12) United States Patent
Cook et al.

(10) Patent No.: US 6,248,554 B1
(45) Date of Patent: Jun. 19, 2001

(54) DNA SEQUENCE CODING FOR A BMP RECEPTOR

(75) Inventors: Jonathan Shaun Cook; Paul Elliott Correa; Jan Susan Rosenbaum, all of Cincinnati; Jerry Ting, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/158,735

(22) Filed: Nov. 24, 1993

(51) Int. Cl.$^7$ .......................... C12P 21/06; C07H 21/04; C12N 15/00; C12N 15/09
(52) U.S. Cl. ................... 435/69.1; 536/23.5; 435/320.1; 435/240.2; 435/252.3; 435/254.11
(58) Field of Search ...................... 536/23, 5; 435/320.1, 435/240.2, 69.1, 252.3, 254.11

(56) References Cited

FOREIGN PATENT DOCUMENTS

94/11502    5/1994   (WO) .............................. C12N/15/12

OTHER PUBLICATIONS

Bonner, T. I., H. Oppermann, P. Seeburg, S. B. Kerby, M. A. Gunnell, A. C. Young and U. R. Rapp, "The Complete Coding Sequence of the Human Raf Oncogene and the Corresponding Structure of the c–raf–1 Gene", Nucleic Acids Res., vol. 14, No. 2, pp. 1009–1015 (Jan. 1986).

Georgi, L. L., P. S. Albert and D. L. Riddle, "Daf–1, A C. Elegans Gene Controlling Dauer Larva Development, Encodes a Novel Receptor Protein Kinase", Cell, vol. 61, No. 4, pp. 635–645 (May 1990).

Mathews, L. S. and W. W. Vale, "Expression Cloning of an Activin Receptor, a Predicted Transmembrane Serine Kinase", Cell, vol. 65, No. 6, pp. 973–982 (Jun. 1991).

Nishida, Y., M. Hata, T. Ayaki, H. Ryo, M. Yamagata, K. Shimizu and Y. Nishizuka, "Proliferation of Both Somatic and Germ Cells is Affected in the Drosophila Mutants of Raf Proto–Oncogene", The EMBO Journal, vol. 7, No. 3, pp. 775–781 (Mar. 1988).

Sumitomo, S., T. Saito and T. Nohno, "A New Receptor Protein Kinase From Chick Embryo Related to Type II Receptor For TGF–β", DNA Sequence—J. DNA Sequence and Mapping, vol. 3, pp. 297–302 (1993).

ten Dijke, P., H. Ichijo, P. Franzén, P. Schulz, J. Saras, H. Toyoshima, C.Heldin and K. Miyazono, "Activin Receptor–like Kinases: A Novel Subclass of Cell–surface Receptors with Predicted Serine/Threonine Kinase Activity", Oncogene, vol. 8, pp. 2879–2887 (Oct. 1993).

Suzuki, A., et al. (1992) Abstracts of the Annual Meeting, Jpn. Mol. Biol. Soc., Abst. No. 2175.

Watson, J. D., et al. (1992) *Recombinant DNA*, New York: Scientific American. Chapters 7 & 12.*

Smith, D. H., et al. (1987) *Science* 238: 1704–07.* ten Dijke, P. P. (1993) GenBank Database Record, Acc. No. Z22135.*

Miyazono, K. (1993) GenBank Database Record, Acc. No. Z23154.*

* cited by examiner

Primary Examiner—Yvonne Eyler
Assistant Examiner—Janet Andres
(74) Attorney, Agent, or Firm—Cynthia M. Bott; Bram J. Corstanje; Karen F. Clark

(57) ABSTRACT

The present invention relates to an isolated BMP receptor kinase protein or soluble fragment thereof, a DNA sequence coding for said BMP receptor kinase protein or said soluble fragment thereof, a recombinant expression vector comprising said DNA sequence, a host cell comprising said recombinant expression vector, a method of expressing said BMP receptor kinase protein or soluble fragment thereof, a method for identifying compounds capable of binding to said BMP receptor kinase protein or soluble fragment thereof, a method for determining the amount of such compounds in a sample, and antibodies to said BMP receptor kinase protein.

26 Claims, 11 Drawing Sheets

Fig. 1

PRIMERS ACT 1A & ACT 1B:

Antisense primers derived from sequence in Kinase Domain VIB:

```
                        A   A      TA   A           A          T
Act1A: 5'-GCG GAA TTC TT AT TCI C  TG  CTI ATI GCI GG  TT-3'
                        G   G      GG   G           C
                        A   A      TA   A           T
Act1B: 5'-GCG GAA TTC TT AT TCI C  TGI G I ATI GCI GG  TT-3'
                        G   G      GG   C           C
```

PRIMERS ACT 2A & ACT 2B

Sense primers derived from sequence in Kinase Domain II:

```
              A                       A  A          A  A
Act2A: 5'-ACT GAA TTC GA  GCI GTI GCI GTI AA    TI TT-3'
              G                       G             G
              A  T                    A  A          A  A
Act2B: 5'-ACT GAA TTC GA  TA  GTI GCI GTI AA    TI TT-3'
              G  C                    G             G
```

```
DAF1      QIRLTGRVGSGRFGNVSRGDYRG    EAVAVKVFNALDEPAFHKETEIFETRMLRHPNVLRYIGSDRV  65
MACT      PLQLLEVKARGRFGCVWKAQLLN    EYVAVKIFPIQDKQSWQNEYEVYSLPGMKHENILQFIGAEKR  65
RTGFBR2   PIELDTLVGKGRFAEVYKAKLKQNTSEQFETVAVKIFPYEEYSSWKTEKDIFSDINLKHENILQFLTAEER  71
MACTR1    QITLLECVGKGRYGEVWRGSWQG    ENVAVKIFSSRDEKSWFRETELYNTVMLRHENILGFIASDMT  65
R3        QVALVECVGKGRYGEVWRGSWHG    ESVAVKIFSSRDEQSWFRETEIYNTVLLRHDNILGFIASDMT  65
R2        TIVLQEIIGKGRFGEVWRGRWRG    GDVAVKIFSSREERSWFREAEIYQTVMLRHENILGFIAADNK  65
R4        TIVLQESIGKGRFGEVWRGKWRG    EEVAVKIFSSREERSWFREAEIYQTVMLRHENILGFIADDNK  65
BRK-1     QIQMVRQVGKGRYGEVWMGKWRG    EKVAVKVFFTTEEASWFRETETIYQTVLMRHENILGFIAADIK  65
T-BRK-1   QIQMVRQVGKGRYGEVWMGKWRG    EKVAVKVFFTTEEASWFRETETIYQTVLMRHENILGFIAADIK  65
```

Fig. 2A

| | | | |
|---|---|---|---|
| DAF1 | DTGFVTELMLVTEYHPSGSLHDFLLENTVNIETYYNLMRSTASGLAFLHNQIGGSKESNKPAMAHRDIKSK | 136 |
| MACT | GTSVDVDLMLITAFHEKGSLSDFLKANVVSWNELCHIAETMARGLAYLHEDIPGLKDGHKPAISHRDIKSK | 136 |
| RTGFBR2 | KTEMGKQYWLITAFHAKGNLQEYLTRHVISWEDLRKLGSSLARGIAHLHSDH TPCGRPKMPIVHRDLKSS | 141 |
| MACTR1 | SRHSSTQLWLITHYHEMGSLYDYLQLTTLDTVSCLRIVLSIASGLAHLHIEI FGTQGKSAIAHRDLKSK | 134 |
| R3 | SRNSSTQLWLITHYHEHGSLYDFLQRQTLEPQLALRLAVSAACGLAHLHVEI FGTQGKPAIAHRDLKSR | 134 |
| R2 | DNGTWTQLMLVSDYHEHGSLFDYLNRYTVTIEGMIKLALSAASGLAHLHMEI VGTQGKPGIAHRDLKSK | 134 |
| R4 | DNGTWTQLMLVSDYHEHGSLFDYLNRYTVTVEGMIKLALSTASGLAHLHMEI VGTQGKPAIAHRDLKSK | 134 |
| BRK-1 | GTGSWTQLYLITDYHENGSLYDFLKCATLDTRALLKLAYSAACGLCHLHTEI YGTQGKPAIAHRDLKSK | 134 |
| T-BRK-1 | GTGSWTQLYLITDYHENGSLYDFLKCATLDTRALLKLAYSAACGLCHLHTEI YGTQGKPAIAHRDLKSR | 134 |

Fig. 2B

| | | | |
|---|---|---|---|
| DAF1 | NIMVKNDLTCAIGDLGLSLSKPEDAASDIIANENYKCGTVRYLAPEILNSTMQFTVFESYQCADVYSFSLV | 207 |
| MACT | NVLLKNNLTACIADFGLAL KFEAGKSAGDTHGQVGTRRYMAPEVLEGAINFQ RDAFLRIDMYAMGLV | 203 |
| RTGFBR2 | NILVKNDLTCCLCDFGLSL RLDPTLSVDDLANSGQVGTARYMAPEVLESRMNLENMESFKQTDVYSMALV | 211 |
| MACTR1 | NILVKKNGQCCIADLGLAV MHSQSTNQLDVGNNPRVGTKRYMAPEVLDETIQVDCFDSYKRVDIWAFGLV | 204 |
| R3 | NVLVKSNLQCCIADLGLAV MHSQSSDYLDIGNNPRVGTKRYMAPEVLDEQIRTDCFESYKWTDIWAFGLV | 204 |
| R2 | NILVKKNGMCAIADLGLAV RHDAVTDTIDIAPNQRVGTKRYMAPEVLDETINMKHFDSFKCADIYALGLV | 204 |
| R4 | NILVKKNGTCCIADLGLAV RHDSATDTIDIAPNHRVGTKRYMAPEVLDDSINMKHFESFKRADIYAMGLV | 204 |
| BRK-1 | NILIKKNGSCCIADLGLAV KFNSDTNEVDIPLNTRVGTKRYMAPEVLDESLNKNHFQPYIMADIYSFGLI | 204 |
| T-BRK-1 | NILIKKNGSCCIADLGLAV KFNSDTNEVDIPLNTRVGTKRYMAPEVLDESLNKNHFQPYIMADIYSFGLI | 204 |

Fig. 2C

| | | |
|---|---|---|
| DAF1 | MWETLCRCEDGDVLPREAATVIPYIEWTDRDPQDAQMFDVVCTRRLRPTENPLMKDHPEMKHIMEIIKTCW | 278 |
| MACT | LWELASRC TAADGPVDEYMLPFEEEIGQHPSLEDMQEVVHKKKRPVLRDYWQKHAGMAMLCETIEECW | 272 |
| RTGFBR2 | LWEMTSRC NAVGEVKDYEPPFGSKVREHPCVESMKDNVLRDRGRPEIPSFWLNHQGIQIVCETLTECW | 279 |
| MACTR1 | LWEVARRM VSNGIVEDYKPPFYDVVPNDPSFEDMRKVVCVDQQRPNIPNRWFSDPTLTSLAKLMKECW | 272 |
| R3 | LWEIARRT IINGIVEDYRPPFYDMVPNDPSFEDMKKVVCVDQQTPTIPNRLAADPVLSGLAQMMRECW | 272 |
| R2 | YWEIARRC NSGGVHEEYQLPYDLVPSDPSIEEMRKVVCDQKLRPNVPNMWQSYEALRVMGKMMRECW | 272 |
| R4 | FWEIARRC SIGGIHEDYQLPYDLVPSDPSVEEMRKVVCEQKLRPNIPNRWQSCEALRVMAKIMRECW | 272 |
| BRK-1 | IWEMARRC ITGGIVEEYQLPYNMVPSDPSYEDMREVVCVKRLRPIVSNRWNSDECLRAVLKLMSECW | 272 |
| T-BRK-1 | IWEMARRC ITGGIVEEYQLPYNMVPSDPSYEDMREVVCVKRLRPIVSNRWNSDEVSW SQVPV K | 268 |

Fig. 2D

```
DAF1     NGNPSARFTSYICRKRMDERQQLLLDKKAKAVAQTAGVTVQDRKILGPQKPKDESPANGA-40 AA  378
MACT     DHDAEARLSAGCVGERITQMQRLTNIITTEDIVTVVTMVINVDFPPKESSL               323
RTGFBR2  DHDPEARLTAQCVAERFSELEHPDRLSGRSCSQEKIPEDGSLNTTK                    325
MACTR1   YQNPSARLTALRIKKTLTKIDNSLDKLKTDC                                   303
R3       YPNPSARLTALRIKKTLQKLSQNPEKPKVIH                                   303
R2       YANGAARLTALRIKKTLSQLSVQEDVKI                                      300
R4       YANGAARLTALRIKKTLSQLSQQEGIKM                                      300
BRK-1    AHNPASRLTALRIKKTLAKMVESQDVKI                                      300
T-BRK-1                                                                    268
```

Fig. 2E

DNA SEQUENCE CODING FOR A BMP RECEPTOR

TECHNICAL FIELD

The present invention relates to the field of bone formation and development. Specifically, the present invention relates to a bone morphogenetic protein receptor and a DNA sequence coding for said receptor.

BACKGROUND

Humans and other warm-blooded animals can be afflicted by a number of bone-related disorders. Such disorders range from bone fractures, to debilitating diseases such as osteoporosis. While in healthy individuals, bone growth generally proceeds normally and fractures heal without the need for pharmacological intervention, in certain instances bones may become weakened or may fail to heal properly. For example, healing may proceed slowly in the elderly and in patients undergoing treatment with corticosteroids (e.g., transplant patients). Osteoporosis is a condition in which bone hard tissue is lost disproportionately to the development of new hard tissue. Osteoporosis can generally be defined as the reduction in the quantity of bone, or the atrophy of skeletal tissue; marrow and bone spaces become larger, fibrous binding decreases, and compact bone becomes fragile. Another bone related disorder is osteoarthritis, which is a disorder of the movable joints characterized by deterioration and abrasion of articular cartilage, as well as by formation of new bone at the joint surface.

While a variety of treatments are available for such bone-related disorders, none of the treatments provide optimum results. One of the difficulties facing individuals who treat bone-related disorders is a lack of complete understanding of bone metabolism and of the bone-related disorders. A key to such understanding is identifying and characterizing each of the components involved in bone growth. Bone morphogenetic proteins (BMPs) have been demonstrated to play a role in bone formation and development (Wozney, J. M., *Molec. Reproduct. and Develop.*, 32: 160–167 (1992)).

Furthermore, the role of BMPs may not be limited to their role in bone. The finding that the BMPs are found at significant concentrations in other tissues such as brain and kidney (Wall, N. A., Blessing, M., Wright, C. V. E., and Hogan, B. L. M., *J Cell Biol.*, 120: 493–502 (1993); Özkaynak, E., Schnegelsberg, P. N. J., Jin, D. F., Clifford, G. M., Warren, F. D., Drier, E. A., and Oppermann, H., *J. Biol. Chem.*, 267: 25220–25227 (1992); Lyons, K. M., Jones, C. M., and Hogan, B. L. M., *Trends in Genetics*, 7: 408–412 (1991)) suggests that they may play additional roles in development and differentiation. In support of this, BMPs have recently been found to promote nerve cell differentiation (Basler, K., Edlund, T., Jessell, T. M., and Yamada, T., *Cell*, 73: 687–702 (1993); Paralkar, V. M., Weeks, B. S., Yu, Y. M., Kleinman, H. K., and Reddi, A. H., *J. Cell Biol.*, 119: 1721–1728 (1992)).

A BMP initiates its biological effect on cells by binding to a specific BMP receptor expressed on the plasma membrane of a BMP-responsive cell. A receptor is a protein, usually spanning the cell membrane, which binds to a ligand from outside the cell, and as a result of that binding sends a signal to the inside of the cell which alters cellular function. In this case, the ligand is the protein BMP, and the signal induces the differentiation of the cell to produce cartilage and bone.

Because of the ability of a BMP receptor to specifically bind BMPs, purified BMP receptor compositions will be useful in diagnostic assays for BMPs, as well as in raising antibodies to the BMP receptor for use in diagnosis and therapy. In addition, purified BMP receptor compositions may be used directly in therapy to bind or scavenge BMPs, thereby providing a means for regulating the bone formation and development activities of BMPs. In order to study the structural and biological characteristics of BMP receptors and the role played by BMPs in the responses of various cell populations to BMPs during bone growth/formation stimulation, or to use a BMP receptor effectively in therapy, diagnosis, or assay, purified compositions of BMP receptor are needed. Such compositions, however, are obtainable in practical yields only by cloning and expressing genes encoding the receptors using recombinant DNA technology. Efforts to purify BMP receptors for use in biochemical analysis or to clone and express mammalian genes encoding BMP receptors have been impeded by lack of a suitable source of receptor protein or mRNA. Prior to the present invention, no cell lines were known to express high levels of BMP receptor constitutively and continuously, which precluded purification of the receptor for protein sequencing or construction of genetic libraries for direct expression cloning. Availability of the BMP receptor sequence will make it possible to generate cell lines with high levels of recombinant BMP receptor for biochemical analysis and use in screening experiments.

Based on the foregoing, there is a need for a BMP receptor DNA sequence and an isolated BMP receptor protein encoded by this sequence.

OBJECTS OF THE INVENTION

It is an object of the present invention to provide an isolated BMP receptor kinase protein.

It is also an object of the present invention to provide a DNA sequence encoding a BMP receptor kinase protein.

It is also an object of the present invention to provide a recombinant expression vector encoding a BMP receptor kinase protein.

It is also an object of the present invention to provide a host cell comprising a recombinant expression vector encoding a BMP receptor kinase protein.

It is also an object of the present invention to provide a method for producing a BMP receptor kinase protein.

It is also an object of the present invention to provide a method for identifying compounds capable of binding to a BMP receptor kinase protein.

It is also an object of the present invention to provide a method for determining the amount of a compound capable of binding a BMP receptor kinase protein in a sample.

It is also an object of the present invention to provide antibodies specific for the BMP receptor protein and a method for producing them.

SUMMARY

The present invention relates to an isolated BMP receptor kinase protein or soluble fragment thereof, a DNA sequence coding for said BMP receptor kinase protein or said soluble fragment thereof, a recombinant expression vector comprising said DNA sequence, a host cell comprising said recombinant expression vector, a method of expressing said BMP receptor kinase protein or soluble fragment thereof, a method for identifying compounds capable of binding to said receptor kinase protein, a method for determining the amount of such compounds in a sample, and antibodies to the said BMP receptor kinase protein or soluble fragment thereof.

BRIEF DESCRIPTION OF THE DRAWINGS

FIG. 1 shows the DNA sequence of the degenerate oligonucleotide primers used in the PCR amplification of BRK-1. The nucleotide bases adenine, thymine, cytosine, guanine, and inosine are represented by the single letter codes A, T, C, G, and I, respectively. ACT1A(SEQ ID NO:7) and ACT1B(SEQ ID NO:8) refer to the set of degenerate 3' PCR primers. ACT2A(SEQ ID NO:9) and ACT2B(SEQ ID NO:10) refer to the set of degenerate 5' PCR primers.

FIGS. 2A, 2B, 2C, 2D and 2E are an alignment of protein sequences comparing the kinase domains of t-BRK-1(SEQ ID NO:2) and BRK-1(SEQ ID NO:4) with other members of the TGF-β receptor family. DAF1(SEQ ID NO:11), the Daf-1 receptor kinase from *C. elegans* (Georgi,. L. L., Albert, P. S., and Riddle, D. L., *Cell*, 61: 635–645 (1990)); MACT(SEQ ID NO:12), mouse activin receptor type II (Mathews, L. S. and Vale, W. W., *Cell*, 65: 973–982 (1991)); RTGFBR2(SEQ ID NO:13), rat TGF-β receptor type II (Tsuchida, K., Lewis, K. A., Mathews, L. S., and Vale, W. W., *Biochem. Biophys. Res. Commun.*, 191: 790–795 (1993)); MACTR1(SEQ ID NO:14), mouse activin receptor type I (Ebner, R., Chen, R.-H., Shum, L., Lawler, S., Zioncheck, T. F., Lee, A., Lopez, A. R., and Derynck, R., *Science*, 260: 1344–1348 (1993)); R3(SEQ ID NO:15); R2(SEQ ID NO:16), and R4(SEQ ID NO:17), type I receptors from rat, ligand unknown (He, W. W., Gustafson, M. L., Hirobe, S., and Donahoe, P. K., *Develop. Dynamics*, 196: 133–142 (1993)). The bracket indicates the predicted kinase termination region for kinases with complete kinase domains.

FIG. 6A, crosslinking of [$^{125}$I]-BMP-4 to BRK-1. Lanes on the left, COS-7 cells transfected with the cDNA for BRK-1, using the construct pJT4-J159F; crosslinking in the absence (–) or presence (+) of 10 nM unlabeled BMP-2. Lanes on the right, mock transfected COS-7 cells; crosslinking in the absence (–) or presence (+) of 10 nM unlabeled BMP-2. FIG. 6B, crosslinking of [$^{125}$I]-DR-BMP-2 to BRK-1. Lanes on the left, COS-7 cells transfected with the cDNA for BRK-1, using the construct pJT4-J159F; crosslinking in the absence (–) or presence (+) of 10 nM unlabeled BMP-2.

DESCRIPTION

Figure 3:
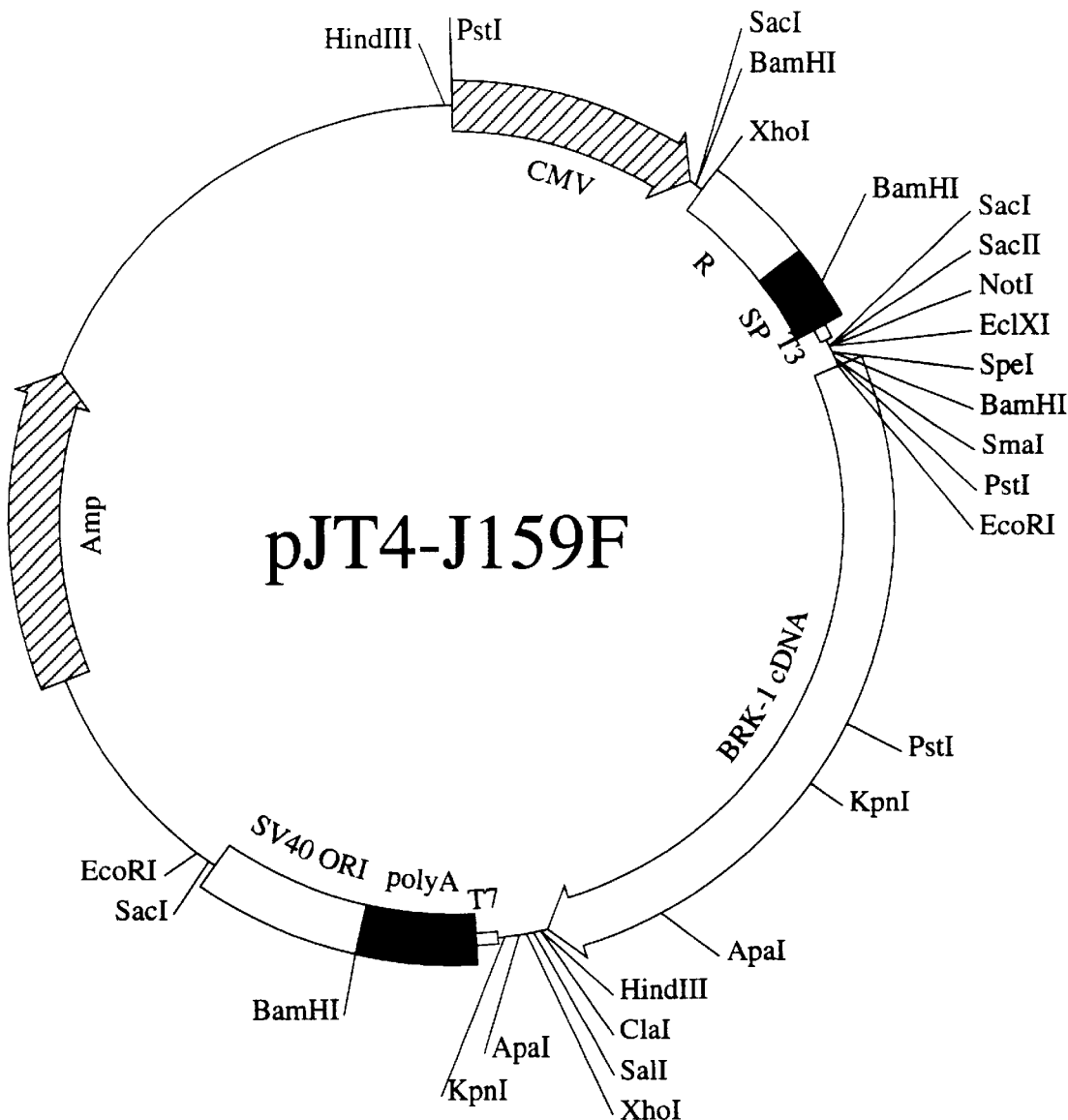
FIG. 3 shows the construct pJT4-J159F, used to express BRK-1 in mammalian cells. CMV, cytomegalovirus early promoter/enhancer; R, the "R" element from the long terminal repeat of human T-cell leukemia virus-1; SP, an intron splice site from the SV40 virus; T3, promoter from the T3 bacteriophage; T7, promoter region from the T7 bacteriophage; poly A, region from the SV40 virus directing polyadenylation of the message; SV40 ORI, origin of replication from the SV40 virus; Amp, ampicillin resistance gene for selection in *E. coli*.

The present invention answers the need for an isolated BMP receptor protein by providing an isolated BMP receptor kinase protein, a DNA sequence coding for said protein, a recombinant expression vector comprising said DNA sequence, a host cell comprising said recombinant expression vector, a method of expressing said BMP receptor kinase protein, and antibodies to said BMP receptor kinase protein.

As used herein, "BMP receptor kinase protein-1" or "BRK-1" means a protein having the amino acid sequence SEQ ID NO:4, as well as proteins having amino acid sequences substantially similar to SEQ ID NO:4 and which are biologically active in that they are capable of binding BMP-2 and/or BMP-4, or transducing a biological signal initiated by a BMP-2 or BMP-4 molecule binding to a cell, or crossreacting with anti-BRK-1 antibodies raised against BRK-1.

As used herein, "truncated BMP receptor kinase protein" or "t-BRK-1" means a protein having amino acid sequence SEQ ID NO:2.

As used herein, "substantially similar" when used to define either amino acid or nucleic acid sequences, means that a particular subject sequence, for example, a sequence altered by mutagenesis, varies from a reference sequence by one or more substitutions, deletions, or additions, the net effect of which is to retain biological activity of the BRK-1 protein. Alternatively, nucleic acid subunits and analogs are "substantially similar" to the specific DNA sequence disclosed herein if the DNA sequences, as a result of degeneracy in the genetic code, encode an amino acid sequence substantially similar to the reference amino acid sequence.

As used herein, "biologically active" means that a particular molecule shares sufficient amino acid sequence similarity with the embodiments of the present invention disclosed herein to be capable of binding detectable quantities of BMP-2 or BMP-4, or transmitting a BMP-2 or BMP-4 stimulus to a cell, for example, as a component of a hybrid receptor construct. Preferably, biologically active BRK-1 or t-BRK-1 within the scope of the present invention is capable of binding [$^{125}$I]-BMP-4 with nanomolar or subnanomolar affinity ($K_d$ approximately equal to $10^{-9}$M). Preferably, the affinity is from about $1 \times 10^{-10}$M to about $1 \times 9^{-9}$M, more preferably about $5 \times 10^{-10}$ M, as per the saturation binding analysis method disclosed in Example 10, below.

As used herein, "soluble fragment" refers to an amino acid sequence corresponding to the extracellular region of BRK-1 or t-BRK-1. Soluble fragments include truncated proteins wherein regions of the receptor molecule not required for BMP binding have been deleted. Examples of such soluble fragments of the present invention include, but are not limited to, polypeptides having the amino acid sequences substantially similar to SEQ ID NO:6, amino acid residues 1–152 depicted in SEQ ID NO:2, amino acid residues 1–152 depicted in SEQ ID NO:4; or polypeptides encoded by nucleic acid residues substantially similar to SEQ ID NO:5, residues 291–746 depicted in SEQ ID NO:1, or residues 11–466 depicted in SEQ ID NO:3.

As used herein, "digit-removed BMP-2" and "DR-BMP-2" refer to a fragment of BMP-2 protein wherein the amino terminus of mature BMP-2 has been removed by mild trypsin digestion.

As used herein, "isolated", in reference to the receptor protein of the present invention or DNA sequences encoding said protein, means that the protein or DNA sequence is removed from the complex cellular milieu in which it naturally occurs, and said protein is expressible from said DNA sequence in a cell that does not naturally express it when operably linked to the appropriate regulatory sequences.

As used herein, "operably linked" refers to a condition in which portions of a linear DNA sequence are capable of influencing the activity of other portions of the same linear DNA sequence. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous in reading frame.

As used herein, "ATCC" means American Type Culture Collection, 12301 Parklavin Drive, Rockville, Md.

As used herein, "bone morphogenetic protein 2" or "BMP-2" means a peptide encoded by a DNA sequence contained in ATCC No. 40345 (see ATCC/NIH REPOSITORY CATALOGUE OF HUMAN AND MOUSE DNA PROBES AND LIBRARIES, sixth Edition, 1992, p. 57, hereinafter "ATCC/NIH REPOSITORY CATALOGUE"). Isolation of BMP is disclosed in U.S. Pat. No. 5,013,649, Wang, Wozney and Rosen, issued May 7, 1991, U.S. Pat. No. 5,166,058, Wang, Wozney and Rosen, issued Nov. 24, 1992; and U.S. Pat. No. 5,168,050, Hammonds and Mason, issued Dec. 1, 1992; each of which is incorporated herein by reference.

As used herein, "bone morphogenetic protein 4" or "BMP-4" means a peptide encoded by a DNA sequence contained in ATCC No. 40342 (see ATCC/NIH REPOSITORY CATALOGUE). Isolation of BMP-4 is disclosed in U.S. Pat. No. 5,013,649, Wang, Wozney and Rosen, issued May 7, 1991, incorporated herein by reference.

As used herein, "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences (introns) which are typically present in eukaryotic genes. Genomic DNA containing the relevant sequences could also be used. Sequences of non-translated DNA may be present 5' or 3' from the open reading frame, where the same do not interfere with manipulation or expression of the coding regions. DNA sequences encoding the proteins provided by this invention can be assembled from cDNA fragments and short oligonucleotide linkers, or from a series of oligonucleotides, to provide a synthetic gene which is capable of being expressed in a recombinant transcriptional unit.

As used herein, "recombinant" means that a protein is derived from a DNA sequence which has been manipulated in vitro and introduced into a host organism.

As used herein, "microbial" refers to recombinant proteins made in bacterial or fungal (e.g., yeast) expression systems.

As used herein, "recombinant expression vector" refers to a DNA construct used to express DNA which encodes BRK-1 or t-BRK-1 and which includes a transcriptional subunit comprising an assembly of 1) genetic elements having a regulatory role in gene expression, for example, promoters and enhancers, 2) a structural or coding sequence which is transcribed into mRNA and translated into protein, and 3) appropriate transcription and translation initiation and termination sequences. Structural elements intended for use in eukaryotic expression systems (e.g. yeast, insect or mammalian cells) preferably include a signal sequence at the N-terminus of the protein enabling transport to the membrane or extracellular secretion of a translated protein by a host cell. Alternatively, where recombinant protein is expressed without a signal sequence, for expression inside the cell, it may include an N-terminal methionine residue. This residue may optionally be subsequently cleaved from the expressed recombinant protein to provide a final product. Using methodology well known in the art, recombinant expression vectors of the present invention can be constructed. Possible vectors for use in the present invention include, but are not limited to: for mammalian cells, pJT4 (discussed further below), pcDNA-1 (Invitrogen, San Diego, Calif.) and pSV-SPORT 1 (Gibco-BRL, Gaithersburg, Md.); for insect cells, pBlueBac III or pBlueBacHis baculovirus vectors (Invitrogen, San Diego, Calif.); and for bacterial cells, pET-3 (Novagen, Madison, Wis.). The DNA sequence coding for BRK-1 or t-BRK-1 can be present in the vector operably linked to regulatory elements. In one embodiment of the present invention, mammalian host cells are preferably transfected with the plasmid construct pJT4-J159F, thereby resulting in expression of BRK-1. In another embodiment of the present invention, mammalian host cells are preferably transfected with the plasmid construct pJT6-J159T, thereby resulting in expression of t-BRK-1. Transfection with the recombinant molecules can be effected using methods well known in the art.

As used herein, "host cell" means a cell comprising a recombinant expression vector of the present invention. Host cells may be stably transfected or transiently transfected within a recombinant expression plasmid or infected by a recombinant virus vector. The host cells include prokaryotic cells, such as *Escherichia coli,* fungal systems such as *Saccharomyces cerevisiae,* permanent cell lines derived from insects such as SF-9 and SF-21, and permanent mammalian cell lines such as Chinese hamster ovary (CHO) and SV40-transformed African green monkey kidney cells (COS).

In one embodiment, the present invention relates to a BMP receptor kinase protein, or soluble fragment thereof. Preferably, the BRK-1 protein has amino acid sequence SEQ ID NO:4. Preferably, the soluble fragment has amino acid sequence SEQ ID. NO:6; preferably the soluble fragment is encoded by nucleic acid sequence SEQ ID NO:5.

In another embodiment, the present invention relates to a DNA sequence coding for the BRK-1 protein. The DNA sequence can be genomic DNA or cDNA. Preferably the DNA sequence is SEQ ID NO:3.

In another embodiment, the present invention relates to a recombinant expression vector comprising a DNA sequence coding for the BRK-1 protein. Preferably the recombinant expression vector is a plasmid having all of the identifying characteristics of the pJT4-J159F plasmid construct contained in ATCC No. 69457.

In another embodiment, the present invention relates to host cells comprising the above described recombinant expression vector. Preferably the host cell is a mammalian cell; more preferably a CHO cell or COS cell.

In another embodiment, the present invention relates to a truncated BMP receptor kinase protein, or soluble fragments thereof. Preferably t-BRK-1 has amino acid sequence SEQ ID NO:2. Preferably the soluble fragment of t-BRK-1 has amino acid sequence SEQ ID NO:6; preferably the soluble fragment of t-BRK-1 is encoded by nucleic acid sequence SEQ ID NO:5.

In another embodiment, the present invention relates to a DNA sequence encoding t-BRK-1. Preferably the DNA sequence encoding t-BRK-1 has SEQ ID NO:1.

In another embodiment, the present invention relates to a recombinant expression vector comprising a DNA sequence coding for t-BRK-1. Preferably the recombinant expression vector is a plasmid having all of the identifying characteristics of the pJT6-J159T plasmid construct contained in ATCC No. 69474.

In another embodiment, the present invention relates to a host cell comprising the recombinant expression vector comprising t-BRK-1. Preferably the host cell is a mammalian cell; more preferably a CHO cell or COS cell.

In another embodiment, the present invention relates to a method for producing BRK-1 or t-BRK-1 comprising isolating BRK-1 or t-BRK-1 from the host cells described above.

In another embodiment, the present invention relates to a method for identifying compounds (e.g., BMP (preferably BMP-2 or BMP-4), and other as yet to be discovered compounds) capable of binding to a BMP receptor kinase protein, the method comprising introducing a sample comprising the compounds to the BMP receptor kinase protein and allowing the compounds to bind to the receptor kinase protein. Preferably the receptor kinase protein has amino acid sequence SEQ ID NO:4 (t-BRK-1) or a soluble fragment thereof, or SEQ ID NO:2 (BRK-1) or soluble fragment thereof. Such a method is also useful for determining the amount of BMP or other receptor binding compound present in the sample.

For example, BMP concentration in a sample could be determined by radioreceptor assay, in which unlabeled BMP in the sample competes with labeled tracer BMP for binding to the BRK-1 or t-BRK-1 receptor. As the amount of BMP in the sample increases, it reduces the amount of labeled BMP which is able to bind to BRK-1 or t-BRK-1. Comparison with a standard curve prepared with known concentrations of unlabeled BMP allows accurate quantitation of BMP concentration in the sample. Labeling of tracer BMP is preferably done by iodination with [$^{125}$I]NaI. BRK-1 or t-BRK-1 can be expressed in the outer membrane of a stable cell line, or supplied as a soluble fragment, or as a soluble fragment covalently attached to a solid support. To perform the assay, unlabeled BMP from the sample and labeled tracer BMP compete for binding to the receptor until equilibrium is reached. The receptor-BMP complex is then isolated from free ligand, for example by washing (in the case of an adherent cell line), rapid filtration or centrifugation (in the case of a nonadherent cell line or receptor bound to a solid support), or precipitation of the receptor-ligand complex with antibodies, polyethylene glycol, or other precipitating agent followed by filtration or centrifugation (in the case of a soluble receptor). The amount of labeled BMP in the complex is then quantitated, typically by gamma counting, and compared to known standards. These methods have been described in the literature using other receptors (Williams, M., *Med. Res. Rev.*, 11:147–184 (1991); Higuchi, M. and Aggarwal, B. B., *Anal. Biochem.*, 204:53–58 (1992); Cain, M. J., R. K, Garlick and P. M. Sweetman, *J. Cardiovasc. Pharm.*, 17:S150–S151 (1991); each of which are incorporated herein by reference), and could readily be adapted to the BRK-1 receptor/BMP system.

The same technique would also be applied in high-throughput screens to identify compounds capable of binding to BRK-1 or t-BRK-1. In such a method, the higher affinity of the compound for BRK-1 or t-BRK-1 (or soluble fragment thereof), the more efficiently it will compete with the tracer for binding to the receptor, and the lower the counts in the receptor-ligand complex. In this case, one would compare a series of compounds at the same concentration range to see which competed for receptor binding with the highest affinity.

In another embodiment, the present invention relates to antibodies specific for BRK-1 or t-BRK-1, and a method for producing the same.

Preferably, for expression of the BRK-1 or t-BRK-1 in systems where the protein product is to be secreted, as in a mammalian cell, the first 23 amino acids of SEQ ID NO:2, SEQ ID NO:4 or SEQ ID NO:6 constitute a signal sequence that directs the protein product to the secretion apparatus of the cell. Subsequently, the protein product will be incorporated into the membrane if a transmembrane domain is present (as in t-BRK-1 (SEQ ID NO:2) or BRK-1(SEQ ID NO:4)), or secreted if no transmembrane domain is present (as in a soluble form of t-BRK-1 or BRK-1(SEQ ID NO:6)). However, the amino acids constituting the signal sequence are generally removed by proteolysis during post-translational processing, so that the mature, processed protein is predicted to start at amino acid Gln 24.

For expression systems where the product is accumulated intracellularly, as in bacteria (e.g., *E coli*), the amino acids constituting the signal sequence would preferably be omitted, and an extra methionine would preferably be added to the N-terminus to serve as a start codon.

This invention is useful for determining whether a ligand, such as a known or putative drug, is capable of binding to and/or activating the BRK-1 receptor encoded by the DNA molecules of the present invention. Transfection of said DNA sequence into the cell systems described herein provides an assay system for the ability of ligands to bind to and/or activate the receptor encoded by the isolated DNA molecule. Recombinant cell lines, such as those described herein, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Soluble receptors derived from the ligand binding domain of the receptor can also be employed in high throughput screening of drug candidates. Functional assays of intracellular signaling can act as assays for binding affinity and efficacy in the activation of receptor function. In addition, the recombinant cell lines may be modified to include a reporter gene operably linked to a response element such that a signal sent by the receptor turns on the reporter gene. Such a system is especially useful in high throughput screens directed at identification of receptor agonists. These recombinant cell lines constitute "drug discovery systems", useful for the identification of natural or synthetic compounds with potential for drug development. Such identified compounds could be further modified or used directly as therapeutic compounds to activate or inhibit the natural functions of the receptor encoded by the isolated DNA molecule.

Stable cell lines expressing high numbers of BRK-1 or a soluble form thereof are also useful as a source of protein for receptor purification. The purified receptor or its soluble form can then be used for high-throughput screening assays for the purposes described above. The purified receptor or its soluble form can also be used for determination of the structure of the BMP: BRK-1 complex, using X-ray crystallography or NMR techniques, which could then be used in rational design of BMP agonists or antagonists.

The nucleotide sequences disclosed herein, SEQ ID NO:1 and SEQ ID NO:3, represent the sequence of t-BRK-1 and BRK-1, respectively, isolated from mouse NIH3T3 cells. These sequences could be readily used to obtain the cDNA for BRK-1 from other species, such as human. These cDNA sequences can also be readily used to isolate the genomic DNA for BRK-1. This would permit analysis of the regulatory elements controlling receptor gene expression, which may offer new opportunities for therapeutic intervention. The nucleotide sequences are also useful to determine the distribution of the BRK-1 in normal tissues and in disease states, which allows an assessment of its physiological role in vivo.

For purposes of illustrating a preferred embodiment of the present invention, the following non-limiting examples are discussed in detail.

EXAMPLE 1

Isolation of the BRK-1 PCR fragment

PCR primers are designed based on an alignment of the protein sequences for the activin (Mathews, L. S. and Vale, W. W., *Cell* 65: 973–982 (1991)) and Daf-1 (Georgi, L. L., Albert, P. S., and Riddle, D. L., *Cell* 61: 635–645 (1990)) receptor kinases, in comparison to the kinase domain sequences of the highly related cytosolic raf protein kinases (Nishida, Y., Hata, M., Toshikazu, A, Ryo, H., Yamagata, M., Shimizu, K.; and Nishizuka, *EMBO J.* 7:775–781 (1988); Bonner, T. L., Oppermann, H., Seeburg, P., Kerby, S. B., Gunnell, M. A., Young, A. C., and Rapp, U. R., *Nucleic Acids Res.* 14: 1009–1015 (1986)). This alignment shows that the activin and Daf-1 receptor kinases contain a unique insert in kinase domain VI that is not present in the raf kinases. Hence, primers are designed to generate fragments that will include this insert and increase the probability of cloning a receptor kinase that is highly related to the activin and Daf-1 receptors. The sense primer is designed as a degenerate oligonucleotide primer that would encode the protein sequence E A/Y V A V K V/I F(SEQ ID NO:18), found in kinase domain II of the activin and Daf-1 receptors. ACT2A and ACT2B are the names assigned to refer to this set of degenerate 5' PCR primers, which are illustrated in FIG. 1. The antisense primer is designed as a degenerate oligonucleotide primer pool that would encode the antisense strand corresponding to protein sequence K P A M/I A/S H R D I K(SEQ ID NO:19), found in domain VIB of the activin and Daf-1 receptors. ACT1A and ACT1B are the names assigned to refer to this set of degenerate 3' PCR primers, which are illustrated in FIG. 1.

Total RNA is isolated from mouse NIH3T3 cells (ATCC CRL 1648) using "RNAZOL" (Tel-Test, Friendswood, Tex.; a solution for rapid isolation of RNA, containing guanidinium thiocyanate, phenol, and β-mercaptoethanol). Poly A+ RNA is then prepared by chromatography on oligo(dT) cellulose chromatography (Pharmacia LKB, Piscataway, N.J.). Single stranded DNA is generated from 200 ng polyadenylated mRNA using reverse transcriptase (first strand synthesis kit from, Stratagene, La Jolla, Calif.; this kit contains components necessary for generating cDNA from RNA, including reverse transcriptase from Maloney murine leukemia virus, primers, nucleotides and buffers). A portion of this material (20%) is then amplified by the polymerase chain reaction (hereinafter PCR) using 50 pmol of the 5' primers ACT2A and ACT2B shown in FIG. 1, and 250 pmol of each of the 3' primers ACT1A and ACT1B shown in FIG. 1. The reaction is run in a 100 µl final volume using the "GENE-AMP" kit (Perkin-Elmer, Norwalk, Conn.; a kit containing components necessary for amplification of DNA using the polymerese chain reaction, including "AMPLITAQ", a recombinant form of the DNA polymerase from *Thermus aquaticus* (Perkin-Elmer, Norwalk, Conn.), nucleotides, and buffers) using a Perkin-Elmer thermal cycler. Standard PCR reaction conditions are used: melting at 94° for 2 min, followed by 35 cycles of melting (94°, 30 sec), annealing (55°, 30 sec), and extension (72° C., 30 sec). After the completion of this first PCR reaction, a 10 µl aliquot of the reaction is removed and subjected to another 35 cycles of amplification with fresh reagents. Products of this secondary PCR are then ligated into the vector pCR 1000 (Invitrogen, San Diego, Calif.) for clonal selection and sequence analysis.

By this method, a PCR fragment of approximately 300 bp is isolated, whose DNA sequence shows a strong homology to the genes for the Daf-1 receptor (Georgi,. L. L., Albert, P. S., and Riddle, D. L., *Cell,* 61: 635–645 (1990)) and mouse activin Type II receptor cDNAs (Mathews, L. S. and Vale, W. W., *Cell,* 65: 973–982 (1991)).

EXAMPLE 2

Isolation of t-BRK-1 DNA

With the PCR fragment in hand, it is next necessary to screen a cDNA library with this fragment in order to isolate a full-length receptor clone.

The PCR fragment is excised, purified by gel electrophoresis, and labeled with ($\alpha$-$^{32}$P)-dCTP, using a random priming method using a "PRIME-IT" Random Primer Labeling Kit (Stratagene, La Jolla, Calif.; a kit containing components necessary for random primer labeling of cDNA, including exonuclease deficient Klenow polymerase, random 9-mer primers, and buffers). The labeled probe is then used to screen a cDNA library prepared from mouse NIH3T3 cells in the vector "λ ZAP II" (Stratagene, La Jolla, Calif.; a lambda cloning vector which accepts inserts up to 10 kb in length and permits automatic excision of inserts in the "pBLUESCRIPT SK(-)" plasmid). Hybridization is performed for 24–48 hours at 42° C. in 5×SSPE (1×SSPE=0.15 M NaCl, 10 mM Na$_2$HPO$_4$, and 1 mM EDTA (ethylenediaminetetraacetic acid)), 1×Denhardt's (0.02% bovine serum albumin, 0.02% polyvinylpyrrolidone, 0.02% Ficoll), 100 µg/ml salmon testis DNA, 50% formamide. Membranes are washed first at 42° C. and subsequently at 55° C. in 0.1×SSPE, and 0.2% sodium dodecyl sulfate (SDS), and the positive plaques identified by autoradiography at −70° C. on "KODAK X-OMAT AR" film (Kodak, Rochester, N.Y.; scientific imaging film) with intensifying screens. Dilution and screening of positive plaques yields an isolated pure phage, which is designated J159#7.

The cloning site in the "λ ZAP II" vector contains the sequence of the plasmid "pBLUESCRIPT SK(-)" (Stratagene, La Jolla, Calif.; a 2.96 kb colony-producing phagemid derived from pUC19). This plasmid sequence, containing the cloned insert, is excised from the purified lambda phage J159#7, using R408 helper phage (Stratagene, La Jolla, Calif.). This yields the t-BRK-1 cDNA subcloned into "pBLUESCRIPT SK(−)". The resulting plasmid, which we designate pBLUESCRIPT-J159T, is suitable for sequence analysis.

EXAMPLE 3 t-BRK-1 Sequence Analysis

The isolated plasmid pBLUESCRIPT-J159T containing the t-BRK-1 cDNA is then sequenced on both strands, using either the "SEQUENASE" Ver. 2.0 kit (U.S. Biochemicals, Cleveland, Ohio; a kit containing components for manual DNA sequencing using the dideoxy terminator method, including "SEQUENASE" (a modified form of T7 DNA polymerase deficient in exonuclease activity, U.S. Biochemicals, Cleveland, Ohio), nucleotide mixes for labeling and extension, dideoxy nucleotide terminators, pyrophosphatase and buffers) or the "TAQ DYE DEOXY" Terminator Cycle Sequencing Kit (Applied Biosystems, Foster City Calif.; a kit containing components for automated DNA sequencing using the dideoxy terminator method, including "AMPLITAQ", nucleotide mix, dye-labeled dideoxy nucleotide terminators, and buffers) with a Model 373A DNA Sequencer (Applied Biosystems, Foster City, Calif.). The complete DNA sequence (SEQ ID NO:1) shows an open reading frame of 1500 base pairs following an initiator ATG.

Comparison of this sequence with the sequence of that of known receptor kinases of the TGF-β family shows a strong homology, but indicates that the kinase domain of t-BRK-1 is considerably shorter than that of related receptor kinases (FIG. 2). Mutational studies on the src kinase have yielded information that specifies the minimal amino acid residues that are necessary at the C terminus of the kinase domain in order for the kinase to function as an active enzyme. Deletions of amino acids upstream of this area yield inactive kinases, presumably because the kinase structure is destabilized (Yaciuk, P. and Shalloway, D., *Molec. and Cell. Biol*, 6: 2807–2819 (1986)). It is therefore generally agreed by those skilled in the art that the end of the kinase domain occurs at a hydrophobic residue located 10 residues downstream of the invariant arginine in kinase domain XI for tyrosine kinases, or 12–18 amino acids downstream of this invariant arginine for serine/threonine kinases, respectively (Hanks, S. K. and Quinn, A. M., *Meth. Enzymol.*, 200: 38–62 (1991)). This region is indicated by the square bracket in FIG. 2. The stop codon in t- BRK-1 is located 20 amino acids prior to the start of the region that specifies the end of the kinase domain, and t-BRK-1 is therefore believed to be a truncated receptor clone. Further analysis of the sequence reveals a putative intact intron-exon junction at position 1763, indicating the possibility that the messenger RNA which served as the template for this cDNA has undergone incomplete post-transcriptional splicing of the RNA, such that a portion of an intron was included in the sequence.

At the N-terminal end of the protein, a eukaryotic signal sequence is identified, with a predicted cleavage site between amino acids 23 and 24 (see SEQ ID NO:2). Thus, after post-translational processing, the mature protein is expected to begin at amino acid Gln24. A region of high hydrophobicity at amino acids 153–176 indicates the presence of a transmembrane region which divides the protein into an extracellular ligand binding domain and an intracellular kinase domain.

EXAMPLE 4

Isolation of BRK-1 DNA

In order to isolate a BRK-1 cDNA that does not include a premature termination in the kinase domain, another cDNA library with a broader representation of mRNA is prepared from NIH3T3 poly A+ RNA (Stratagene, La Jolla, Calif.). This library, constructed in "UNI-ZAP XR" (Stratagene, La Jolla, Calif.; a lambda cloning vector which allows construction of unidirectional cDNA libraries) uses both a poly dT sequence and a random primer for the synthesis of the cDNA library. This library is then screened with the J159 PCR fragment, labeled with $^{32}P$ by the random priming method ("PRIME-IT" Random Primer Labeling Kit). Screening and isolation of clones is carried out as described above (Example 2). Several additional clones are obtained and subjected to sequence analysis.

EXAMPLE 5

BRK-1 Sequence Analysis

Sequence analysis of the clones is carried out using the "TAQ DYE DEOXY" Terminator Cycle Sequencing Kit and the Applied Biosystems Model 373A DNA Sequencer (Applied BioSystems, Foster City, Calif.). Comparison of the clones to the sequence of t-BRK-1 and to other receptor kinases (FIG. 2) indicates that one clone (SEQ ID NO:3) contains the full length coding sequence, with no intron present, and the complete kinase domain. The plasmid from this clone is designated pBLUESCRIPT-J159F. The open reading frame is 1596 base pairs encoding a protein with 532 amino acids, with a predicted molecular mass of about 60,059. This cDNA is designated as BRK-1.

The DNA sequence of BRK-1 is identical to that of t-BRK-1 over nucleotides 1–1483 in SEQ ID NO:3 (nucleotides 281–1763 in SEQ ID NO:1), and hence identical in amino acid sequence over amino acids 1–491 in SEQ ID NO:4 and SEQ ID NO:2. Thus, the N-terminal signal sequence and the transmembrane domain observed in t-BRK-1 and described in Example 3 are identically present in full length BRK-1. The entire ligand binding domain is also identical. The nucleotide sequence for t-BRK-1 (SEQ ID NO:1) contains a 90 base pair insert (nucleotides 1764≧1853) which is absent in the nucleotide sequence of BRK-1 (SEQ ID NO:3), which may represent a portion of an incompletely spliced intron. After this point, nucleotides 1854–2035 of the t-BRK-1 sequence are identical to nucleotides 1484–1665 of the BRK-1 sequence. Hence, removal of the 90 base pair insert in t-BRK-1 yields a coding sequence identical to that of BRK-1.

EXAMPLE 6

Generation of Antibodies to BRK-1

In order to demonstrate expression of the BRK-1 receptor, to demonstrate ligand binding, and to identify other proteins which may complex with BRK-1, the availability of antibodies specific for the receptor is highly useful. Polyclonal antisera are accordingly produced in rabbits for this purpose, using two antigens.

First, the mature extracellular ligand binding domain, comprising amino acids 24–152 of SEQ ID NO:2 (or amino acids 24–152 of SEQ ID NO:4), is expressed in *E. coli* using the "QIA EXPRESS" bacterial expression system (Qiagen, Chatsworth, Calif.; a kit for high-level expression of proteins in *E. coli*, which incorporates into the protein an affinity tag of six histidines to allow rapid purification of the recombinant protein by metal chelate chromatography; the kit includes pQE-12 expression vector, a plasmid encoding the lac repressor, *E coli* host strains and metal chelate resin). A portion of the nucleotide sequence, comprising nucleotides 360–746 in SEQ ID NO:1 (or nucleotides 80 to 466 in SEQ ID NO:3), is amplified by the polymerase chain reaction using primers which incorporate Bgl II sites at the 5' and 3' ends. Specifically, the primer for the 5' end is CCATAGATCTCAGAATCTAGATAGT(SEQ ID NO:20), and for the 3' end is GGTAAGATCTTCGGATCCTGCCATC(SEQ ID NO:21). The amplified insert is inserted into the PQE12 vector (Qiagen, Chatsworth, Calif.), which directs the expression of the insert with six histidines at the C terminal end of the protein. After transformation of E. coli strain JM101 with this construct, the transformed strain is grown in LB broth supplemented at mid-log phase with isopropyl thio-β-galactoside (IPTG), which induces expression of the protein driven by the lac promoter. Three hours after addition of IPTG, cells are harvested by centrifugation and lysed in a "FRENCH" pressure cell (SLM-Aminco, Urbana, Ill.; a dispersion unit for disintegrating bacteria under high pressure using a hydraulic press) using two passes at 16,000 psi. The extracellular domain is purified by chromatography on a nickel metal chelate column, according to the manufacturer's instructions. Further purification is attained by chromatography on a preparative C4 reverse phase column (Waters DeltaPak C4 column, 300 Å, 7.8 mm×30 cm, Millipore, Milford, Mass.), using a linear gradient of 0.05% TFA (trifluoroacetic acid) in water to 0.05% TFA in 80% acetonitrile, over 90 minutes at a flow rate of 2.8 ml/min. Peak fractions eluting at 38% acetonitrile are pooled, dried under vacuum, and used to immunize three New Zealand White rabbits (Hazleton Washington, Vienna, Va.). Antisera are evaluated by Western blots for their ability to detect the purified E. coli antigen. The antiserum with the highest titer is designated 1353.

A second antigen, intended to recognize the intracellular kinase domain, is generated from a peptide having an identical amino acid sequence to amino acids 398–420 of SEQ ID NO:4 (or amino acids 398–420 of SEQ ID NO:2), with the addition of a cysteine at the C terminus to permit conjugation of the peptide; i.e., indicated by the single letter amino acid abbreviations, LNTRVGTKRYMAPEVLDESLNKNC(SEQ ID NO:22). Comparison of the amino acid sequence of the kinase domain of BRK-1 with the kinase domain of the Raf protein suggests that this region of BRK-1 corresponds to a region of the Raf kinase which was used to make highly specific antibodies (Kolch, W., Weissinger, E., Mischak, H., Troppmair, J., Showalter, S. D., Lloyd, P., Heidecker, G., and Rapp, U. R. *Oncogene* 5: 713–720 (1990)). This peptide is conjugated by standard methods to keyhole limpet hemocynanin, and used to immunize three New Zealand White rabbits (Hazleton Washington, Vienna, Va.). The resulting antisera are evaluated for their ability to recognize the original peptide coated on plastic, using an antibody capture ELISA (enzyme-linked immunosorbent assay). The antisera are designated 1378, 1379, and 1380.

EXAMPLE 7

Expression of BRK-1

In order to identify the function of BRK-1, it is necessary to express the protein and test to see whether it binds a specific ligand. This is preferably done in a mammalian cell line, since this maximizes the chance of expressing a correctly processed protein in the cell membrane. To this end, the BRK-1 cDNA is subcloned into the expression vector pJT4 to generate the plasmid pJT4-J159F. The BRK-1 insert from pBLUESCRIPT-J159F is digested with the restriction endonuclease Alf III, generating a linearized plasmid with a single overhang. The overhanging end is filled in using DNA Polymerase I Kienow fragment, generating a blunt end. The linearized plasmid is then digested with Not I, liberating the insert from the plasmid. The pJT4 expression vector is digested with Not I and EcoRV, and ligated to the insert. The blunt end generated by the Klenow reaction is compatible with the EcoRV site, which is also a blunt end; ligation eliminates the Eco RV site. The resulting construct is shown in FIG. 3.

The pJT4 vector, optimized for transient expression in COS cells, includes the cytomegalovirus early promoter and enhancer, which gives very efficient transcription of message; an "R" element from the long terminal repeat of the human T-cell leukemia virus-1, which has been shown to increase expression levels further (Takebe, Y., M. Seiki, J.-I. Fujisawa, P. Hoy, K. Yokota, M. Yoshida and N. Arai, *Mol. Cell. Biol.*, 8:466–472 (1988)); an intron splice site from SV40, which is believed to enhance message stability; a multiple cloning site; a polyadenylation signal derived from SV40, which directs the addition of a poly A tail to the message, as is required for most eukaryotic mRNA; and the SV40 origin of replication, which permits the replication of the plasmid to extremely high copy number in cells which contain the SV40 large T antigen, such as COS cells. In addition, for manipulation and amplification of the vector in bacteria, the vector contains an E. coli origin of replication and an ampicillin resistance gene.

Transient expression of BRK-1 using pJT4-J159F is carried out in COS-7 cells (ATCC CRL 1651) using electroporation. Cells are grown to confluence in DME (Dulbecco's Modified Eagle) high glucose media supplemented with 5% fetal bovine serum (Hyclone, Logan, Utah), nonessential amino acids (GIBCO, Gaithersburg, Md.), and glutamine, then trypsinized to release cells from the plate. The detached cells are pelleted in a tabletop centrifuge, then resuspended in fresh media at a concentration of $6.25 \times 10^6$ cells/ml. The cell suspension ($5 \times 10^6$ cells, 0.8 ml) is transferred to the cuvette from a BioRad "GENE PULSER" electroporation system (BioRad, Hercules, Calif.). The purified DNA plasmid (10 μg) is added to the cuvette, and the cells subjected to electoporation at 4.0 kV/cm, with a capacitance of 25 μFd. Cells are then plated and allowed to recover. Fresh media is supplied after 24 hr. At 48 hr, cells are ready to be tested for binding of BMP-4.

EXAMPLE 8

Expression of t-BRK-1

Figure 4:
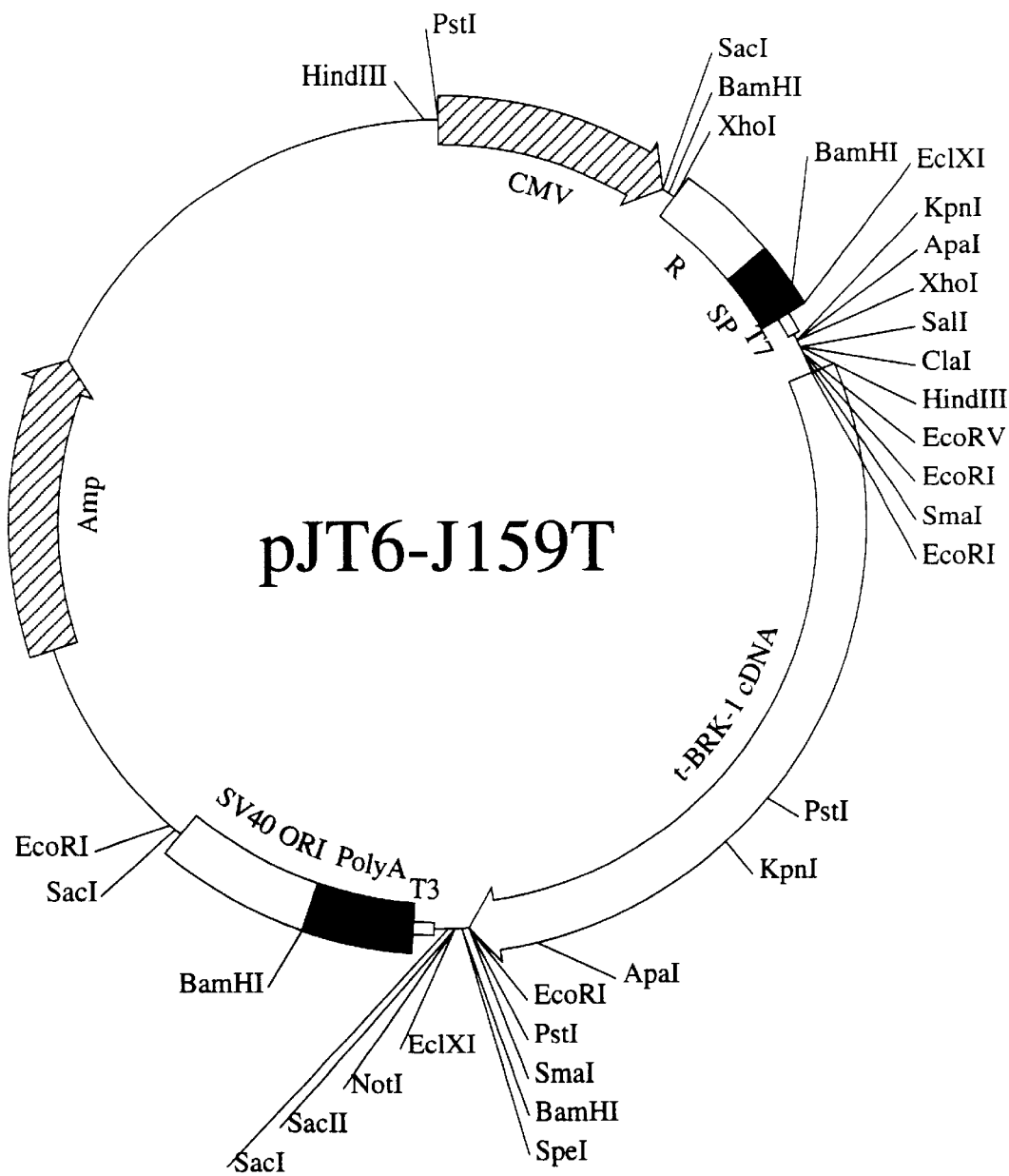
FIG. 4 shows the construct pJT6-J159T, used to express t-BRK-1 in mammalian cells. Abbreviations are the same as those in FIG. 3.

For expression of t-BRK-1, the cDNA insert from pBLUESCRIPT-J159T is excised using the restriction endonucleases Not I and Xho I, and subcloned into the Not I and Sal I sites of the expression vector pJT6, generating the construct pJT6-J159T shown in FIG. 4. The vector pJT6 is identical to pJT4, described in Example 6, except for the opposite orientation of the multiple cloning site, and the presence of a spacer DNA between the Pst I and Bam H1 sites of the multiple cloning region.

Transient expression of t-BRK-1 in COS cells using the pJT6-J159T construct is carried out exactly as described above for BRK-1 (Example 7).

EXAMPLE 9

Preparation of radiolabeled BMP ligands

The preferred radioligand in all these studies is BMP-4. BMP-4 is labeled with $^{125}$I by the chloramine-T method (Frolik, C. A., Wakefield, L. M., Smith, D. M., and Sporn, M. B. *J. Biol. Chem.* 259: 10995–11000 (1984)). BMP-4 (2 µg) is taken up in 5 µl of 30% acetonitrile, 0.1% trifluoracetic acid (TFA) plus an additional 5 µl of 1.5 M sodium phosphate, pH 7.4. Carrier free [$^{125}$I] (1 mCi, 4–10 µl) is added, together with 2 µl of a chloramine T solution (100 µg/ml). An additional 2 µl of the chloramine T solution is added at 2.0 min and at 3.5 min. After 4.5 minutes, the reaction is stopped by the addition of 10 µl of 50 mM N-acetyl tyrosine, 100 µl of 60 mM potassium iodide, and 100 µl of 11M urea in 1 M acetic acid. After a 3.5 minute incubation, unreacted iodine is removed on a PD-10 gel filtration column (Pharmacia, Piscataway, N.J.) run in 4 mM HCl, 75 mM NaCl, 1 mg/ml bovine serum albumin (BSA). The resulting labeled protein is >95% precipitable by trichloroacetic acid, indicating that all [$^{125}$I] is protein bound, and has a typical specific activity of 3000–8000 Ci/mmol.

BMP-2 can be radiolabeled in the same manner and used as a radioligand. However, use of BMP-2 results in very high nonspecific binding, presumably because of binding of BMP-2 to extracellular matrix proteins. Such nonspecific binding can be significantly reduced, and hence the usefulness of BMP-2 as a radioligand significantly improved, by removal of amino terminus of the protein, presumably because this removes the region responsible for binding to the extracellular matrix. Removal of the amino terminus from BMP-2 can be accomplished by partial proteolysis with trypsin (Wozney, J. M., *Mol. Rep. Dev.*, 32:160–167 (1992)). This yields a derivative designated "digit-removed BMP-2", or DR-BMP-2. Preparation and purification of DR-BMP-2 is carried out as follows.

BMP-2 (100–250 µg) is solubilized in 500 µl of 4 M urea, 0.1 M NaCl, 0.05 M Tris-HCl (pH 8.2). Trypsin (Sequencing Grade; Boehringer Mannheim, Indianapolis, Ind.) is added to a trypsin/BMP-2 ratio of 1/50 (w/w), and the digestion mixture is incubated at 37° C. for 2 hr. Digestion is stopped by the addition of phenylmethylsulfonylfluoride (PMSF) to a final concentration of 1 mM, and the mixture is frozen and stored at –20° C. until purification.

DR-BMP-2 is purified from the digestion mixture by reversed phase HPLC (high performance liquid chromatography) on a Waters Delta-Pak C4 column (5 µm, 300 A, 3.9×150 mm; Millipore Corp., Milford, Mass.). The entire digestion mixture is injected directly onto the column, and DR-BMP-2 is eluted using a linear gradient from 0.05% TFA to 0.05% TFA, 60% acetonitrile over 80 min. at a flow rate of 0.7 ml/min. The majority of DR-BMP-2 elutes as a well-defined peak at about 36% acetonitrile, as monitored by absorbance at 214 nm and after Coomassie blue staining of an SDS-polyacrylamide gel. PMSF, PMSF-inactivated trypsin, and any remaining intact BMP-2 are separated from DR-BMP-2 under these chromatographic conditions. Purified DR-BMP-2 is aliquoted, taken to dryness under vacuum, and stored at –20° C.

Analysis by SDS-polyacrylamide gel electrophoresis shows that the molecular weight of DR-BMP-2 is decreased by approximately 2000 daltons compared to BMP-2 under nonreduced conditions, and by about 1000 daltons under reducing conditions. Amino-terminal protein sequencing demonstrates that roughly 70% of DR-BMP-2 begins at Lys290, while the remaining 30% begins at Leu292. Results from amino acid analysis are entirely consistent with the sequencing results and suggest that the COOH-terminus of the protein is unaffected by trypsin treatment. Radiolabeling of DR-BMP-2 is carried out exactly as described for BMP-4.

EXAMPLE 10

BMP Binding to BRK-1

Binding of DR-BMP-2 and BMP-4 to BRK-1 can be demonstrated by three separate methods: whole cell binding of radiolabeled BMP; covalent crosslinking of radiolabeled BMP to the receptor; and immunoprecipitation of the receptor crosslinked to labeled ligand. These three methods are described in detail below.

For whole cell binding experiments, COS-7 cells are transfected with pJT4-J159F as described in example 7. After electroporation, cells are seeded in 12 well plates at 670,000 cells/ell. Media is changed after 24 hr, and binding experiments are carried out at 48 hr. At that time, cells are washed once with binding buffer (50 mM Hepes buffer, pH 7.4, 128 mM NaCl, 5 mM KCl, 5 mM MgSO$_4$, 1.2 mM CaCl$_2$, 2 mg/ml BSA), then equilibrated in the same buffer at 4° C. for 30 min with gentle shaking. The buffer is then aspirated, and to each well is added 500 µl of binding buffer (4° C.), containing [$^{125}$I]-BMP-4 tracer (100 pM), as well as varying concentrations of unlabeled BMP-2, BMP-4, or other unlabeled ligand, depending on the assay. For determination of nonspecific binding, BMP-2 is added to the binding buffer at a final concentration of 10 nM. To prevent degradation of ligand during the incubation, a protease inhibitor cocktail is also added, to give a final concentration of 10 µg/ml leupeptin, 10 µg/ml antipain, 50 µg/ml aprotinin, 100 µg/ml benzamidine, 100 µg/ml soybean trypsin inhibitor, 10 µg/ml bestatin, 10 µg/ml pepstatin, and 300 µM PMSF. The cells are incubated for 4 hr at 4° C. with gently shaking. At the end of the incubation period, the buffer is aspirated, and the cells are rinsed 4 times with 1 ml washing buffer (50 mM HEPES, pH 7.4, 128 mM NaCl, 5 mM KCl, 5 mM MgSO$_4$, 1.2 mM CaCl$_2$, 0.5 mg/ml BSA). After the final wash is aspirated, 750 µl, of solubilization buffer (10 mM TrisCl pH 7.4, 1 mM EDTA, 1% (v/v) Triton X-100) is added to each well and incubated at room temperature for 15 min. The solubilized cells are then transferred to fresh tubes and counted in a Packard Model 5005 "COBRA" Gamma Counter (Packard Instrument Co., Downers Grove, Ill.).

Figure 5:
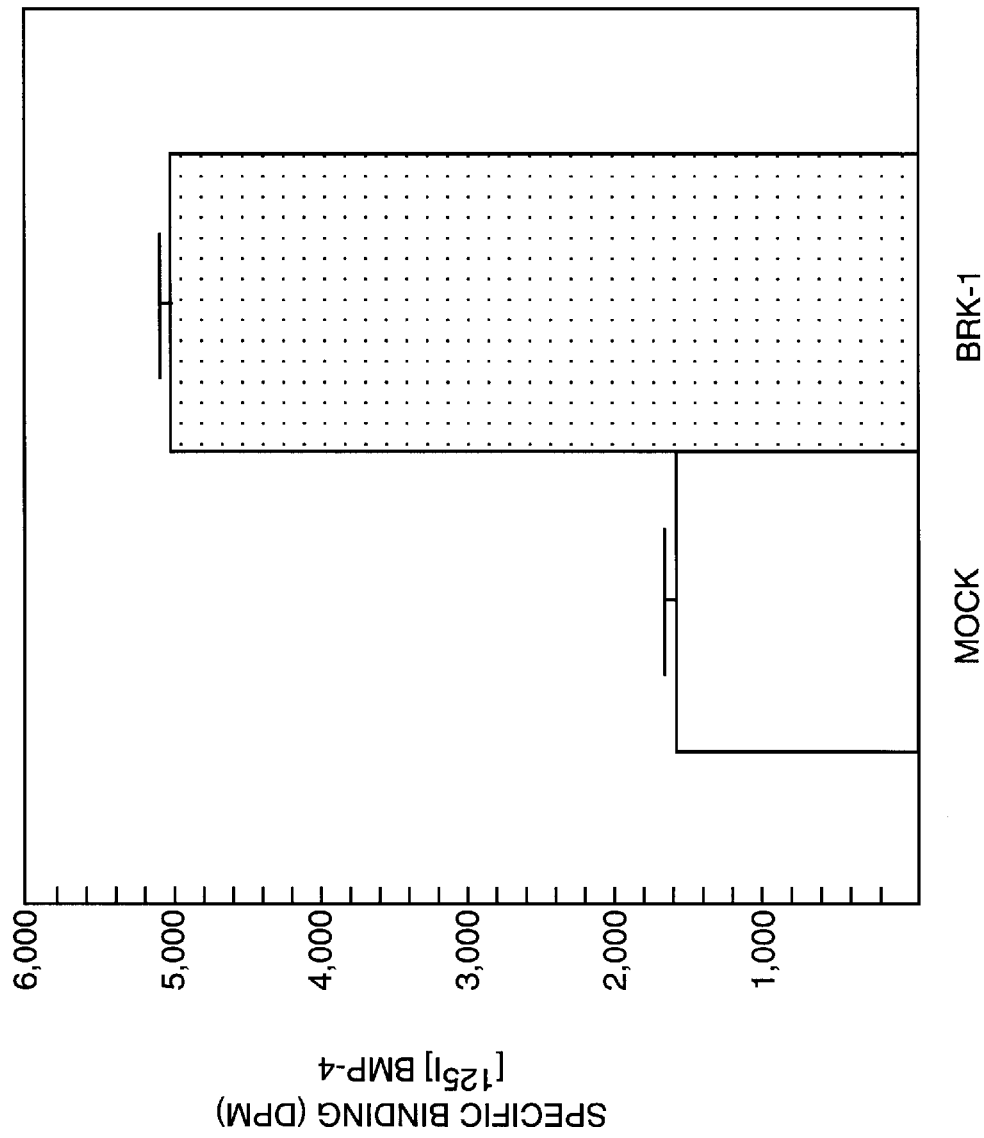
FIG. 5 shows binding of [$^{125}$I]-BMP-4 to COS-7 cells transfected with the cDNA for BRK-1, using the construct pJT4-J159F. The concentration of [$^{125}$I]-BMP-4 is 100 pM.

Results of such an experiment are shown in FIG. 5. Specific binding of [$^{125}$I]-BMP-4 to COS-7 cells transfected with the cDNA to BRK-1 (using the construct pJT4-J159F) is three times higher than binding to mock-transfected COS-7 cells.

In order to obtain a more quanitative characterization of binding to BRK-1, a saturation binding analysis is performed on COS-7 cells transfected with the cDNA for BRK-1, using the construct pJT4-J159F. Binding of [$^{125}$I]-BMP-4 is examined over a concentration range of 10–1000 pM, with nonspecific binding determined with 10 nM unlabeled BMP-4. Binding data was analyzed using LIGAND software (Version 3.0; Elsevier-Biosoft, Cambridge, UK) to obtain an affinity (K$_d$) for BRK-1 of 5×10$^{-10}$ M, well within the physiological range expected for a BMP receptor.

A second method of demonstrating binding of BMPs to BRK-1 is to crosslink the radiolabeled ligand to the BRK-1 receptor. In this method, the bifunctional crosslinking reagent disuccinimidyl suberate (DSS) (Pierce Chemical, Rockford, Ill.) is used to covalently crosslink bound radiolabeled ligand to its receptor by reaction with free amino groups on lysine residues in the two proteins. Following the crosslinking, cellular proteins are separated by gel electrophoresis, and radioactive bands visualized. The labeled bands represent the receptor selectively "tagged" with the radiolabeled ligand. In this procedure, cells are transfected with pJT4-J159F as described in example 7, then seeded into 12 well plates at 670,000 cells/well. Media is changed after 24 hr. At 48 hr after electroporation, the cells are washed, equilibrated, and incubated with [$^{125}$I]-BMP-4 or [$^{125}$I]-DRBMP-2 and competing unlabeled ligands as described in this example for whole cell binding studies.

After completion of the 4 hour incubation with ligand, the cells are washed three times at 4° C. with 2 ml of binding buffer having the same composition as described above, except that no BSA is added. To each well is then added 1 ml of fresh BSA-free binding buffer, followed by freshly prepared DSS to a final concentration of 135 μM. After swirling gently to mix the DSS, the plates are incubated for exactly 15 minutes at 4° C. with gentle shaking. At this point the media is aspirated and the cells washed with 3 ml detachment buffer (10 mM Tris, 0.25 M sucrose, 1 mM EDTA, 0.3 mM PMSF, pH 7.4). An additional 0.75 ml detachment buffer is added to each well; the cells are scraped off into the buffer and transferred to fresh microcentrifuge tubes. Each well is then rinsed with an additional 0.5 ml detachment buffer, which is added to the corresponding tube. The samples are centrifuged (13,000×g, 15 min) and the supernatant discarded. The pellets are taken up in 20 μL reducing sample buffer (125 mM TrisCl pH 6.8, 1% β-mercaptoethanol, 2% SDS, 0.1% bromphenol blue, 10% glycerol), vortexed for 30–45 min at 4° C., boiled for 5 minutes, and centrifuged (13,0000×g, 5 min). The supernatants are loaded onto 7.5% SDS-polyacrylamide gels and subjected to electrophoresis. The gels are stained in 0.12% Coomassie Blue, 5% methanol, 7.5% acetic acid, destained in 5% methanol, 7.5% acetic acid, then dried between sheets of cellophane. Radioactivity on the dried gel is visualized and quantitated on a PhosphorImager (Molecular Devices, Sunnyvale, Calif.), or subjected to autoradiography using "KODAK X-OMAT AR" film (Kodak Rochester, N.Y.).

Figure 6A:
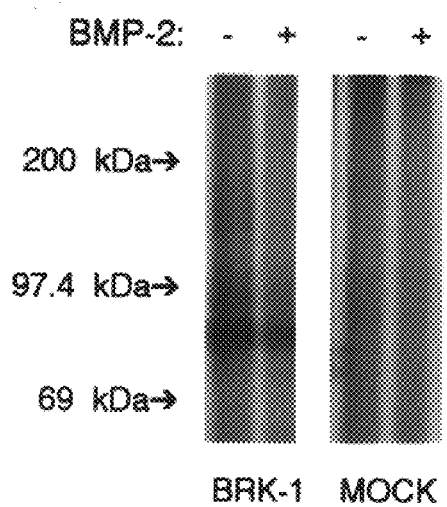
FIG. 6A and FIG. 6B show crosslinking of radiolabelled BMPs to COS-7 cells transfected with the cDNA for BRK-1.
Figure 6B:
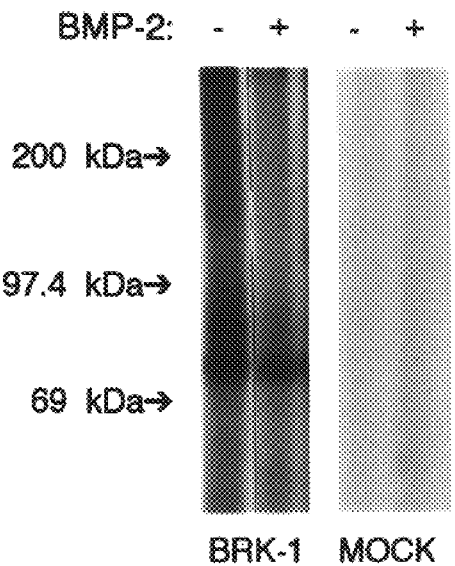

Result of such experiments are shown in FIG. 6. FIG. 6A shows crosslinking of [$^{125}$I]-BMP-4 to COS-7 cells transfected with BRK-1 using the construct pJT4-J159F. In lane 1, note the presence of a labeled band at molecular weight 76,800 which corresponds to BRK-1 covalently crosslinked to BMP-4. This band is greatly reduced by the addition of 10 nM BMP-2 to the cells during incubation and is absent in mock-transfected COS cells. This indicates specific binding of BMP-4 to BRK-1. Since the labeled band represents the receptor covalently crosslinked to BMP-4 (monomer molecular weight 16,400), the molecular weight of the receptor can be estimated at 60,400, which is consistent with the amino acid sequence of BRK-1. FIG. 6B shows the same experiment using [$^{125}$I]-DRBMP-2 as the ligand. A similar labeled band is observed. As with [$^{125}$I]-BMP-4, the labeled band is greatly reduced by the addition of 10 nM BMP-2 to the cells and is absent in mock transfected cells. Taken together, these data indicate that both BMP-2 and BMP-4 are specifically bound by BRK-1.

In a third demonstration of BMP binding to BRK-1, COS cells transfected with the cDNA for BRK-1 are first crosslinked to [$^{125}$I]-BMP-4, then subjected to immunoprecipitation with antibodies specific for BRK-1. In this procedure, COS-7 cells are transfected with pJT-J159F as described in Example 7 and plated into 100 mm dishes seeded at 1×10$^7$ cell/dish. They are then crosslinked to [125I]-BMP-4 as described in this example, except that the incubation with [$^{125}$I]-BMP-4 and unlabeled ligand is carried out in a total of 4 ml, instead of 500 μl, and all other volumes are increased accordingly. Following the crosslinking, cells are washed three times with ice-cold PBS [phosphate buffered saline], then lysed with 4 ml of RIP buffer (20 mM TrisCl, pH 8.0, 100 mM NaCl, 1 mM Na$_2$EDTA, 0.5% Nonidet P-40, 0.5% sodium deoxycholate, 10 mM sodium iodide, and 1% bovine serum albumin). The lysate is centrifuged in a Beckman GPR tabletop centrifuge at 3500 rpm (3000×g) for 10 min. The supernatant is transferred to a fresh tube and made 0.1 % in SDS. To remove any existing antibody present in the lysate, 200 μl of "PANSORBIN" (Calbiochem, La Jolla, Calif.; a 10% solution of *Staphylococcus aureus*) is added. After a 30 minute incubation at 4° C, the lysate is centrifuged as before, and the supernatant again transferred to a fresh tube, split into aliquots as required.

The primary antibody—1353, for the extracellular domain; or 1378, 1379, or 1380, for the kinase domain—is then added to the tube at a final dilution of 1:100, and incubated for 2 hr on ice. To precipitate the complex of antigen: primary antibody, 50 μl of "PANSORBIN" is then added and incubated 30 min on ice. The complex is pelleted at 3500 rpm (3000×g) for 10 min in a Beckman GPR centrifuge (Beckman Instruments, Fullerton, Calif.) and the supernatant discarded. The pellet is washed three times in RIP buffer containing 0.1% SDS, and once in TNEN buffer (20 mM Tris, pH 8.0, 100 mM NaCl, 1 mM EDTA, 0.5% NP-40). The pellet is resuspended in 25 μl of reducing sample buffer. Solubilized proteins are subjected to electrophoresis is SDS polyacrylamide gels and autoradiography as described above for crosslinking experiments.

Figure 7:
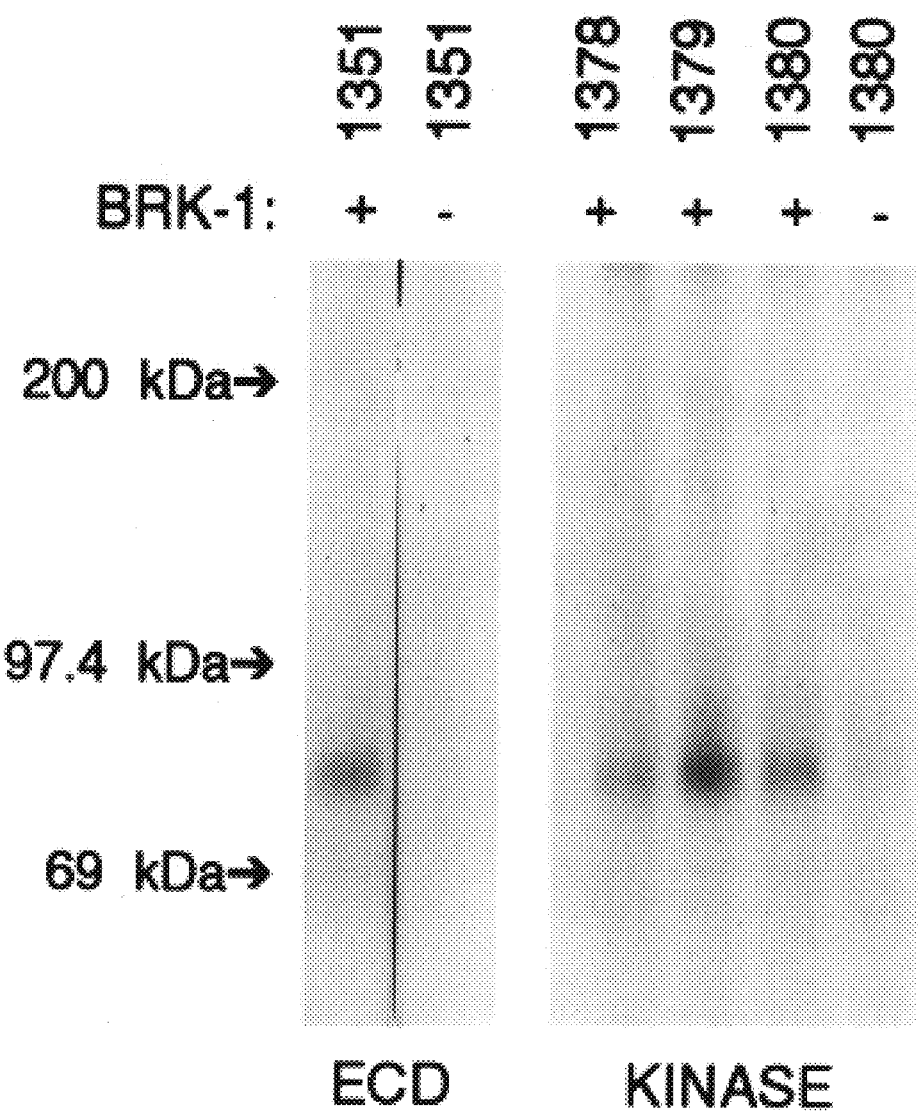
FIG. 7 shows immunoprecipitation of BRK-1 expressed in COS-7 cells and crosslinked to [$^{125}$I]-BMP-4. Lanes designated "+", COS-7 cells transfected with the cDNA for BRK-1, using the construct pJT4-J159F. Lanes designated "–", mock-transfected COS-7 cells. After transfection, cells were crosslinked to [$^{125}$I]-BMP-4, then subjected to immunoprecipitation using the indicated antisera. Lanes on the left, antiserum 1351, specific for the extracellular domain (ECD); lanes on the right, antisera 1378, 1379, and 1380, all specific for the kinase domain.

Results of such an experiment are shown in FIG. 7. Antibodies to both the extracellular domain (lane 1) and the intracellular domain (lanes 3–5) precipitate a band of molecular weight of approximately 81,000. Subtracting the monomer weight of BMP-4 (16,400), the molecular weight of the receptor is estimated at 64,000, similar to the result obtained in the crosslinking experiments described above. All three antisera to the intracellular domain precipitate the same protein. This characteristic band is absent in mock-transfected cells (lanes 2 and 6). This experiment demonstrates that the crosslinked labeled band observed in crosslinking experiments, such as those shown in FIG. 6, is immunologically related to BRK-1, because it is precipitated by four separate antibodies specific for BRK-1.

Deposit of t-BRK-1 and BRK-1

*E. coli* transformed with pJT6-J159T (SEQ ID NO:1 subcloned into expression vector pJT6) was deposited with the ATCC on Oct. 20, 1993, and assigned ATCC Designation No. 69474.

*E. coli* transformed with pBLUESCRIPT-J159T (SEQ ID NO:1 subcloned into expression vector "pBLUESCRIPT SK(-)") was deposited with the ATCC on Oct. 7, 1993, and assigned ATCC Designation No. 69458.

*E. coli* transformed with pJT4-J159F (SEQ ID NO:3 subcloned into expression vector pJT4) was deposited with the ATCC on Oct. 7, 1993, and assigned ATCC Designation No. 69457.

As is recognized in the art, there are occasionally errors in DNA and amino acid sequencing methods. As a result, the sequences encoded in the deposited material are controlling in the event of an error in any of the sequences found in the written description of the present invention. It is further noted that one of ordinary skill in the art reproducing Applicants' work from the written disclosure can discover any sequencing errors using routine skill. The deposit of ATCC No. 69457 and ATCC No. 69474 is not to be considered as an admission that the deposited material is essential to the practice of the present invention.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claim is:

1. An isolated DNA sequence coding for a BMP receptor kinase protein having amino acid sequence SEQ ID NO:4.

2. The DNA sequence of claim 1, wherein the DNA sequence is SEQ ID NO:3.

3. An isolated DNA sequence coding for a truncated BMP receptor kinase protein having amino acid sequence SEQ ID NO:2.

4. The DNA sequence of claim 3, wherein the DNA sequence is SEQ ID NO:1.

5. A DNA sequence coding for a soluble fragment of a BMP receptor kinase protein, the soluble fragment having amino acid sequence SEQ ID NO:6.

6. The DNA sequence of claim 5, wherein the DNA sequence is SEQ ID NO:5.

7. A recombinant expression vector comprising the DNA sequence of claim 1.

8. A recombinant expression vector comprising the DNA sequence of claim 2.

9. A recombinant expression vector comprising the DNA sequence of claim 3.

10. A recombinant expression vector comprising the DNA sequence of claim 4.

11. A host cell comprising the recombinant expression vector of claim 7.

12. A host cell comprising the recombinant expression vector of claim 8.

13. A host cell comprising the recombinant expression vector of claim 9.

14. A host cell comprising the recombinant expression vector of claim 10.

15. The mammalian host cell of claim 14, wherein the cell is a Chinese hamster ovary cell.

16. The mammalian host cell of claim 14, wherein the cell is a COS cell.

17. A method for producing BMP receptor kinase protein comprising culturing the host cell of claim 11 in a manner allowing expression of the BMP receptor kinase protein and isolation of the BMP receptor kinase protein.

18. A method for producing truncated BMP receptor kinase protein comprising culturing the host cell of claim 12 in a manner allowing expression of the truncated BMP receptor kinase protein and isolation of the BMP receptor kinase protein.

19. A plasmid having all of the identifying characteristics of pJT4-J159F contained in ATCC No. 69457.

20. An isolated DNA sequence coding for a BMP receptor kinase protein encoded by the plasmid of claim 19.

21. A mammalian host cell comprising the plasmid of claim 20.

22. The mammalian host cell of claim 21, wherein the cell is a Chinese hamster ovary cell.

23. The mammalian host cell of claim 21, wherein the cell is a COS cell.

24. A plasmid having all of the identifying characteristics of pJT6-J159T contained in ATCC No. 69474.

25. An isolated DNA sequence coding for a BMP receptor kinase protein encoded by the plasmid of claim 24.

26. A mammalian host cell comprising the plasmid of claim 24.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
       (A) LENGTH: 2056 base pairs
       (B) TYPE: nucleic acid
       (C) STRANDEDNESS: double
       (D) TOPOLOGY: linear (ix) FEATURE:
       (A) NAME/KEY: CDS
       (B) LOCATION: join(291..1790)

(xi) SEQUENCE DESCRIPTION: SEQ ID NO: 1:

```
CGAATTCCTC GCGCCGTGGG AGGGGCGGCC CGGCCCACCC CCACGCCCCG CCCGGGAGGG      60

ACGGGGGGAG AGAGAGCGCG GCGACGGGTA TCTGGGTCAA AGCTGTTCGG AGAAATTGGA     120

ACTACAGTTT TATCTAGCCA CATCTCTGAG AATTCTGAAG AAAGCAGCAG GTGAAAGTCA     180

TTGCCAAGTG ATTTTGTTCT GTAAGGAAGC CTCCCTCATT CACTTACACC AGTGAGACAG     240

CAGGACCAGT CATTCAAAGG GCCGTGTACA GGACGCGTGC GAATCAGACA ATG ACT        296
                                                       Met Thr
                                                         1

CAG CTA TAC ACT TAC ATC AGA TTA CTG GGA GCC TGT CTG TTC ATC ATT       344
Gln Leu Tyr Thr Tyr Ile Arg Leu Leu Gly Ala Cys Leu Phe Ile Ile
          5                  10                  15

TCT CAT GTT CAA GGG CAG AAT CTA GAT AGT ATG CTC CAT GGC ACT GGT       392
Ser His Val Gln Gly Gln Asn Leu Asp Ser Met Leu His Gly Thr Gly
 20                  25                  30

ATG AAA TCA GAC TTG GAC CAG AAG AAG CCA GAA AAT GGA GTG ACT TTA       440
Met Lys Ser Asp Leu Asp Gln Lys Lys Pro Glu Asn Gly Val Thr Leu
 35                  40                  45                  50

GCA CCA GAG GAT ACC TTG CCT TTC TTA AAG TGC TAT TGC TCA GGA CAC       488
Ala Pro Glu Asp Thr Leu Pro Phe Leu Lys Cys Tyr Cys Ser Gly His
             55                  60                  65

TGC CCA GAT GAT GCT ATT AAT AAC ACA TGC ATA ACT AAT GGC CAT TGC       536
Cys Pro Asp Asp Ala Ile Asn Asn Thr Cys Ile Thr Asn Gly His Cys
         70                  75                  80

TTT GCC ATT ATA GAA GAA GAT GAT CAG GGA GAA ACC ACA TTA ACT TCT       584
Phe Ala Ile Ile Glu Glu Asp Asp Gln Gly Glu Thr Thr Leu Thr Ser
             85                  90                  95

GGG TGT ATG AAG TAT GAA GGC TCT GAT TTT CAA TGC AAG GAT TCA CCG       632
Gly Cys Met Lys Tyr Glu Gly Ser Asp Phe Gln Cys Lys Asp Ser Pro
100                 105                 110

AAA GCC CAG CTA CGC AGG ACA ATA GAA TGT TGT CGG ACC AAT TTG TGC       680
Lys Ala Gln Leu Arg Arg Thr Ile Glu Cys Cys Arg Thr Asn Leu Cys
115                 120                 125                 130

AAC CAG TAT TTG CAG CCT ACA CTG CCC CCT GTT GTT ATA GGT CCG TTC       728
Asn Gln Tyr Leu Gln Pro Thr Leu Pro Pro Val Val Ile Gly Pro Phe
                135                 140                 145

TTT GAT GGC AGC ATC CGA TGG CTG GTT GTG CTC ATT TCC ATG GCT GTC       776
Phe Asp Gly Ser Ile Arg Trp Leu Val Val Leu Ile Ser Met Ala Val
                150                 155                 160

TGT ATA GTT GCT ATG ATC ATC TTC TCC AGC TGC TTT TGC TAT AAG CAT       824
Cys Ile Val Ala Met Ile Ile Phe Ser Ser Cys Phe Cys Tyr Lys His
            165                 170                 175

TAT TGT AAG AGT ATC TCA AGC AGG GGT CGT TAC AAC CGT GAT TTG GAA       872
```

```
Tyr Cys Lys Ser Ile Ser Ser Arg Gly Arg Tyr Asn Arg Asp Leu Glu
    180             185                 190

CAG GAT GAA GCA TTT ATT CCA GTA GGA GAA TCA TTG AAA GAC CTG ATT         920
Gln Asp Glu Ala Phe Ile Pro Val Gly Glu Ser Leu Lys Asp Leu Ile
195             200             205                 210

GAC CAG TCC CAA AGC TCT GGG AGT GGA TCT GGA TTG CCT TTA TTG GTT         968
Asp Gln Ser Gln Ser Ser Gly Ser Gly Ser Gly Leu Pro Leu Leu Val
                215             220                 225

CAG CGA ACT ATT GCC AAA CAG ATT CAG ATG GTT CGG CAG GTT GGT AAA        1016
Gln Arg Thr Ile Ala Lys Gln Ile Gln Met Val Arg Gln Val Gly Lys
            230             235             240

GGC CGC TAT GGA GAA GTA TGG ATG GGT AAA TGG CGT GGT GAA AAA GTG        1064
Gly Arg Tyr Gly Glu Val Trp Met Gly Lys Trp Arg Gly Glu Lys Val
        245             250             255

GCT GTC AAA GTG TTT TTT ACC ACT GAA GAA GCT AGC TGG TTT AGA GAA        1112
Ala Val Lys Val Phe Phe Thr Thr Glu Glu Ala Ser Trp Phe Arg Glu
    260             265             270

ACA GAA ATC TAC CAG ACG GTG TTA ATG CGT CAT GAA AAT ATA CTT GGT        1160
Thr Glu Ile Tyr Gln Thr Val Leu Met Arg His Glu Asn Ile Leu Gly
275             280             285                 290

TTT ATA GCT GCA GAC ATT AAA GGC ACT GGT TCC TGG ACT CAG CTG TAT        1208
Phe Ile Ala Ala Asp Ile Lys Gly Thr Gly Ser Trp Thr Gln Leu Tyr
                295             300                 305

TTG ATT ACT GAT TAC CAT GAA AAT GGA TCT CTC TAT GAC TTC CTG AAA        1256
Leu Ile Thr Asp Tyr His Glu Asn Gly Ser Leu Tyr Asp Phe Leu Lys
            310             315                 320

TGT GCC ACA CTA GAC ACC AGA GCC CTA CTC AAG TTA GCT TAT TCT GCT        1304
Cys Ala Thr Leu Asp Thr Arg Ala Leu Leu Lys Leu Ala Tyr Ser Ala
        325             330             335

GCT TGT GGT CTG TGC CAC CTC CAC ACA GAA ATT TAT GGT ACC CAA GGG        1352
Ala Cys Gly Leu Cys His Leu His Thr Glu Ile Tyr Gly Thr Gln Gly
    340             345             350

AAG CCT GCA ATT GCT CAT CGA GAC CTG AAG AGC AAA AAC ATC CTT ATT        1400
Lys Pro Ala Ile Ala His Arg Asp Leu Lys Ser Lys Asn Ile Leu Ile
355             360             365                 370

AAG AAA AAT GGA AGT TGC TGT ATT GCT GAC CTG GGC CTA GCT GTT AAA        1448
Lys Lys Asn Gly Ser Cys Cys Ile Ala Asp Leu Gly Leu Ala Val Lys
                375             380                 385

TTC AAC AGT GAT ACA AAT GAA GTT GAC ATA CCC TTG AAT ACC AGG GTG        1496
Phe Asn Ser Asp Thr Asn Glu Val Asp Ile Pro Leu Asn Thr Arg Val
            390             395                 400

GGC ACC AAG CGG TAC ATG GCT CCA GAA GTG CTG GAT GAA AGC CTG AAT        1544
Gly Thr Lys Arg Tyr Met Ala Pro Glu Val Leu Asp Glu Ser Leu Asn
        405             410             415

AAA AAC CAT TTC CAG CCC TAC ATC ATG GCT GAC ATC TAT AGC TTT GGT        1592
Lys Asn His Phe Gln Pro Tyr Ile Met Ala Asp Ile Tyr Ser Phe Gly
420             425             430

TTG ATC ATT TGG GAA ATG GCT CGT CGT TGT ATT ACA GGA GGA ATC GTG        1640
Leu Ile Ile Trp Glu Met Ala Arg Arg Cys Ile Thr Gly Gly Ile Val
435             440             445                 450

GAG GAA TAT CAA TTA CCA TAT TAC AAC ATG GTG CCC AGT GAC CCA TCC        1688
Glu Glu Tyr Gln Leu Pro Tyr Tyr Asn Met Val Pro Ser Asp Pro Ser
                455             460             465

TAT GAG GAC ATG CGT GAG GTT GTG TGT GTG AAA CGC TTG CGG CCA ATC        1736
Tyr Glu Asp Met Arg Glu Val Val Cys Val Lys Arg Leu Arg Pro Ile
            470             475             480

GTG TCT AAC CGC TGG AAC AGC GAT GAA GTA AGT TGG AGC CAA GTC CCT        1784
Val Ser Asn Arg Trp Asn Ser Asp Glu Val Ser Trp Ser Gln Val Pro
        485             490             495
```

-continued

```
GTA AAG TGATGAGTGA GTGCCGAGTT ACTCTGTGCT CACCACACTC TGTTTGCATT      1840
Val Lys
    500

TATTTCTCTT TAGTGTCTTC GAGCAGTTTT GAAGCTAATG TCAGAATGTT GGGCCCATAA   1900

TCCAGCCTCC AGACTCACAG CTTTGAGAAT CAAGAAGACA CTTGCAAAAA TGGTTGAATC   1960

CCAGGATGTA AAGATTTGAC AATTAAACAA TTTTGAGGGA GAATTTAGAC TGCAAGAACT   2020

TCTTCACCCA AGGAAGGAAT TCCTGCAGGC CCGGGG                             2056
```

(2) INFORMATION FOR SEQ ID NO: 2:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Gln Leu Tyr Thr Tyr Ile Arg Leu Leu Gly Ala Cys Leu Phe
  1               5                  10                  15

Ile Ile Ser His Val Gln Gly Gln Asn Leu Asp Ser Met Leu His Gly
                 20                  25                  30

Thr Gly Met Lys Ser Asp Leu Asp Gln Lys Lys Pro Glu Asn Gly Val
             35                  40                  45

Thr Leu Ala Pro Glu Asp Thr Leu Pro Phe Leu Lys Cys Tyr Cys Ser
         50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Val Leu Ile Ser Met
145                 150                 155                 160

Ala Val Cys Ile Val Ala Met Ile Ile Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
```

```
                    290                 295                 300
Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
                355                 360                 365

Leu Ile Lys Lys Asn Gly Ser Cys Cys Ile Ala Asp Leu Gly Leu Ala
370                 375                 380

Val Lys Phe Asn Ser Asp Thr Asn Glu Val Asp Ile Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
                435                 440                 445

Ile Val Glu Glu Tyr Gln Leu Pro Tyr Tyr Asn Met Val Pro Ser Asp
450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Val Ser Trp Ser Gln
                485                 490                 495

Val Pro Val Lys
            500

(2) INFORMATION FOR SEQ ID NO: 3:

(i) SEQUENCE CHARACTERISTICS:
          (A) LENGTH: 2402 base pairs
          (B) TYPE: nucleic acid
          (C) STRANDEDNESS: double
          (D) TOPOLOGY: linear (ix) FEATURE:
          (A) NAME/KEY: CDS
          (B) LOCATION: join(11..1606)

(xi) SEQUENCE DESCRIPTION: SEQ ID NO: 3:

GAATCAGACA ATG ACT CAG CTA TAC ACT TAC ATC AGA TTA CTG GGA GCC         49
           Met Thr Gln Leu Tyr Thr Tyr Ile Arg Leu Leu Gly Ala
             1               5                  10

TGT CTG TTC ATC ATT TCT CAT GTT CAA GGG CAG AAT CTA GAT AGT ATG        97
Cys Leu Phe Ile Ile Ser His Val Gln Gly Gln Asn Leu Asp Ser Met
     15                  20                  25

CTC CAT GGC ACT GGT ATG AAA TCA GAC TTG GAC CAG AAG AAG CCA GAA       145
Leu His Gly Thr Gly Met Lys Ser Asp Leu Asp Gln Lys Lys Pro Glu
 30                  35                  40                  45

AAT GGA GTG ACT TTA GCA CCA GAG GAT ACC TTG CCT TTC TTA AAG TGC       193
Asn Gly Val Thr Leu Ala Pro Glu Asp Thr Leu Pro Phe Leu Lys Cys
                 50                  55                  60

TAT TGC TCA GGA CAC TGC CCA GAT GAT GCT ATT AAT AAC ACA TGC ATA       241
Tyr Cys Ser Gly His Cys Pro Asp Asp Ala Ile Asn Asn Thr Cys Ile
             65                  70                  75

ACT AAT GGC CAT TGC TTT GCC ATT ATA GAA GAA GAT GAT CAG GGA GAA       289
Thr Asn Gly His Cys Phe Ala Ile Ile Glu Glu Asp Asp Gln Gly Glu
         80                  85                  90
```

```
ACC ACA TTA ACT TCT GGG TGT ATG AAG TAT GAA GGC TCT GAT TTT CAA      337
Thr Thr Leu Thr Ser Gly Cys Met Lys Tyr Glu Gly Ser Asp Phe Gln
         95                  100                 105

TGC AAG GAT TCA CCG AAA GCC CAG CTA CGC AGG ACA ATA GAA TGT TGT      385
Cys Lys Asp Ser Pro Lys Ala Gln Leu Arg Arg Thr Ile Glu Cys Cys
110             115                 120                 125

CGG ACC AAT TTG TGC AAC CAG TAT TTG CAG CCT ACA CTG CCC CCT GTT      433
Arg Thr Asn Leu Cys Asn Gln Tyr Leu Gln Pro Thr Leu Pro Pro Val
                130                 135                 140

GTT ATA GGT CCG TTC TTT GAT GGC AGC ATC CGA TGG CTG GTT GTG CTC      481
Val Ile Gly Pro Phe Phe Asp Gly Ser Ile Arg Trp Leu Val Val Leu
            145                 150                 155

ATT TCC ATG GCT GTC TGT ATA GTT GCT ATG ATC ATC TTC TCC AGC TGC      529
Ile Ser Met Ala Val Cys Ile Val Ala Met Ile Ile Phe Ser Ser Cys
                160                 165                 170

TTT TGC TAT AAG CAT TAT TGT AAG AGT ATC TCA AGC AGG GGT CGT TAC      577
Phe Cys Tyr Lys His Tyr Cys Lys Ser Ile Ser Ser Arg Gly Arg Tyr
        175                 180                 185

AAC CGT GAT TTG GAA CAG GAT GAA GCA TTT ATT CCA GTA GGA GAA TCA      625
Asn Arg Asp Leu Glu Gln Asp Glu Ala Phe Ile Pro Val Gly Glu Ser
190                 195                 200                 205

TTG AAA GAC CTG ATT GAC CAG TCC CAA AGC TCT GGG AGT GGA TCT GGA      673
Leu Lys Asp Leu Ile Asp Gln Ser Gln Ser Ser Gly Ser Gly Ser Gly
                210                 215                 220

TTG CCT TTA TTG GTT CAG CGA ACT ATT GCC AAA CAG ATT CAG ATG GTT      721
Leu Pro Leu Leu Val Gln Arg Thr Ile Ala Lys Gln Ile Gln Met Val
            225                 230                 235

CGG CAG GTT GGT AAA GGC CGC TAT GGA GAA GTA TGG ATG GGT AAA TGG      769
Arg Gln Val Gly Lys Gly Arg Tyr Gly Glu Val Trp Met Gly Lys Trp
        240                 245                 250

CGT GGT GAA AAA GTG GCT GTC AAA GTG TTT TTT ACC ACT GAA GAA GCT      817
Arg Gly Glu Lys Val Ala Val Lys Val Phe Phe Thr Thr Glu Glu Ala
255                 260                 265

AGC TGG TTT AGA GAA ACA GAA ATC TAC CAG ACG GTG TTA ATG CGT CAT      865
Ser Trp Phe Arg Glu Thr Glu Ile Tyr Gln Thr Val Leu Met Arg His
270                 275                 280                 285

GAA AAT ATA CTT GGT TTT ATA GCT GCA GAC ATT AAA GGC ACT GGT TCC      913
Glu Asn Ile Leu Gly Phe Ile Ala Ala Asp Ile Lys Gly Thr Gly Ser
                290                 295                 300

TGG ACT CAG CTG TAT TTG ATT ACT GAT TAC CAT GAA AAT GGA TCT CTC      961
Trp Thr Gln Leu Tyr Leu Ile Thr Asp Tyr His Glu Asn Gly Ser Leu
            305                 310                 315

TAT GAC TTC CTG AAA TGT GCC ACA CTA GAC ACC AGA GCC CTA CTC AAG     1009
Tyr Asp Phe Leu Lys Cys Ala Thr Leu Asp Thr Arg Ala Leu Leu Lys
        320                 325                 330

TTA GCT TAT TCT GCT GCT TGT GGT CTG TGC CAC CTC CAC ACA GAA ATT     1057
Leu Ala Tyr Ser Ala Ala Cys Gly Leu Cys His Leu His Thr Glu Ile
335                 340                 345

TAT GGT ACC CAA GGG AAG CCT GCA ATT GCT CAT CGA GAC CTG AAG AGC     1105
Tyr Gly Thr Gln Gly Lys Pro Ala Ile Ala His Arg Asp Leu Lys Ser
350                 355                 360                 365

AAA AAC ATC CTT ATT AAG AAA AAT GGA AGT TGC TGT ATT GCT GAC CTG     1153
Lys Asn Ile Leu Ile Lys Lys Asn Gly Ser Cys Cys Ile Ala Asp Leu
                370                 375                 380

GGC CTA GCT GTT AAA TTC AAC AGT GAT ACA AAT GAA GTT GAC ATA CCC     1201
Gly Leu Ala Val Lys Phe Asn Ser Asp Thr Asn Glu Val Asp Ile Pro
            385                 390                 395

TTG AAT ACC AGG GTG GGC ACC AAG CGG TAC ATG GCT CCA GAA GTG CTG     1249
Leu Asn Thr Arg Val Gly Thr Lys Arg Tyr Met Ala Pro Glu Val Leu
```

```
                400                 405                    410
GAT GAA AGC CTG AAT AAA AAC CAT TTC CAG CCC TAC ATC ATG GCT GAC    1297
Asp Glu Ser Leu Asn Lys Asn His Phe Gln Pro Tyr Ile Met Ala Asp
        415                 420                 425

ATC TAT AGC TTT GGT TTG ATC ATT TGG GAA ATG GCT CGT CGT TGT ATT    1345
Ile Tyr Ser Phe Gly Leu Ile Ile Trp Glu Met Ala Arg Arg Cys Ile
430                 435                 440                 445

ACA GGA GGA ATC GTG GAG GAA TAT CAA TTA CCA TAT TAC AAC ATG GTG    1393
Thr Gly Gly Ile Val Glu Glu Tyr Gln Leu Pro Tyr Tyr Asn Met Val
                450                 455                 460

CCC AGT GAC CCA TCC TAT GAG GAC ATG CGT GAG GTT GTG TGT GTG AAA    1441
Pro Ser Asp Pro Ser Tyr Glu Asp Met Arg Glu Val Val Cys Val Lys
            465                 470                 475

CGC TTG CGG CCA ATC GTG TCT AAC CGC TGG AAC AGC GAT GAA TGT CTT    1489
Arg Leu Arg Pro Ile Val Ser Asn Arg Trp Asn Ser Asp Glu Cys Leu
        480                 485                 490

CGA GCA GTT TTG AAG CTA ATG TCA GAA TGT TGG GCC CAT AAT CCA GCC    1537
Arg Ala Val Leu Lys Leu Met Ser Glu Cys Trp Ala His Asn Pro Ala
    495                 500                 505

TCC AGA CTC ACA GCT TTG AGA ATC AAG AAG ACA CTT GCA AAA ATG GTT    1585
Ser Arg Leu Thr Ala Leu Arg Ile Lys Lys Thr Leu Ala Lys Met Val
510                 515                 520                 525

GAA TCC CAG GAT GTA AAG ATT TGACAATTAA ACAATTTTGA GGGAGAATTT       1636
Glu Ser Gln Asp Val Lys Ile
                530

AGACTGCAAG AACTTCTTCA CCCAAGGAAT GGGTGGGATT AGCATGGAAT AGGATGTTGA  1696

CTTGGTTTCC AGACTCCTTC CTCTACATCT TCACAGGCTG CTAACAGTAA ACCTTACCGC  1756

ACTCTACAGA ATACAAGATT GGAACTTGGA ACTTGGAACT TCAAACATGT CATTCTTTAT  1816

ATATGGACAG CTGTGTTTTA AATGTGGGGT TTTTGTGTTT TGCTTTCTTT GTTTTGTTTT  1876

GGTTTTGATG CTTTTTTGGT TTTTATGAAC TGCATCAAGA CTCCAATCCT GATAAGAAGT  1936

CTCTGGTCAA CCTCTGGGTA CTCACTATCC TGTCCATAAA GTGGTGCTTT CTGTGAAAGC  1996

CTTAAGAAAA TTAATGAGCT CAGCAGAGAT GGAAAAGGC ATATTTGGCT TCTACCAGAG   2056

AAAACATCTG TCTGTGTTCT GTCTTTGTAA ACAGCCTATA GATTATGATC TCTTTGGGAT  2116

ACTGCCTGGC TTATGATGGT GCACCATACC TTTGATATAC ATACCAGAAT TCTCTCCTGC  2176

CCTAGGGCTA AGAAGACAAG AATGTAGAGG TTGCACAGGA GGTATTTTGT GACCAGTGGT  2236

TTAAATTGCA ATATCTAGTT GGCAATCGCC AATTTCAAA AAGCCATCCA CCTTGTAGCT    2296

GTAGTAACTT CTCCACTGAC TTTATTTTTA GCATAATAGT TGTGAAGGCC AAACTCCATG  2356

TAAAGTGTCC ATAGACTTGG ACTGTTTTCC CCCAGCTCTG ATTACC                 2402

(2) INFORMATION FOR SEQ ID NO: 4:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO: 4:

Met Thr Gln Leu Tyr Thr Tyr Ile Arg Leu Leu Gly Ala Cys Leu Phe
 1               5                  10                  15

Ile Ile Ser His Val Gln Gly Gln Asn Leu Asp Ser Met Leu His Gly
            20                  25                  30

Thr Gly Met Lys Ser Asp Leu Asp Gln Lys Lys Pro Glu Asn Gly Val
```

-continued

```
            35                  40                  45
Thr Leu Ala Pro Glu Asp Thr Leu Pro Phe Leu Lys Cys Tyr Cys Ser
             50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Gln Gly Glu Thr Thr Leu
                     85                  90                  95

Thr Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Cys Arg Thr Asn
                115                 120                 125

Leu Cys Asn Gln Tyr Leu Gln Pro Thr Leu Pro Pro Val Val Ile Gly
            130                 135                 140

Pro Phe Phe Asp Gly Ser Ile Arg Trp Leu Val Val Leu Ile Ser Met
145                 150                 155                 160

Ala Val Cys Ile Val Ala Met Ile Ile Phe Ser Ser Cys Phe Cys Tyr
                165                 170                 175

Lys His Tyr Cys Lys Ser Ile Ser Ser Arg Gly Arg Tyr Asn Arg Asp
                180                 185                 190

Leu Glu Gln Asp Glu Ala Phe Ile Pro Val Gly Glu Ser Leu Lys Asp
                195                 200                 205

Leu Ile Asp Gln Ser Gln Ser Ser Gly Ser Gly Ser Gly Leu Pro Leu
            210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
                260                 265                 270

Arg Glu Thr Glu Ile Tyr Gln Thr Val Leu Met Arg His Glu Asn Ile
                275                 280                 285

Leu Gly Phe Ile Ala Ala Asp Ile Lys Gly Thr Gly Ser Trp Thr Gln
            290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
                355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Ile Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
450                 455                 460
```

```
Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
                500                 505                 510

Thr Ala Leu Arg Ile Lys Lys Thr Leu Ala Lys Met Val Glu Ser Gln
                515                 520                 525

Asp Val Lys Ile
        530
```

(2) INFORMATION FOR SEQ ID NO: 5:

(i) SEQUENCE CHARACTERISTICS:
        (A) LENGTH: 466 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: join(11..466)

(xi) SEQUENCE DESCRIPTION: SEQ ID NO: 5:

```
GAATCAGACA ATG ACT CAG CTA TAC ACT TAC ATC AGA TTA CTG GGA GCC        49
           Met Thr Gln Leu Tyr Thr Tyr Ile Arg Leu Leu Gly Ala
             1               5                  10

TGT CTG TTC ATC ATT TCT CAT GTT CAA GGG CAG AAT CTA GAT AGT ATG        97
Cys Leu Phe Ile Ile Ser His Val Gln Gly Gln Asn Leu Asp Ser Met
         15                  20                  25

CTC CAT GGC ACT GGT ATG AAA TCA GAC TTG GAC CAG AAG AAG CCA GAA       145
Leu His Gly Thr Gly Met Lys Ser Asp Leu Asp Gln Lys Lys Pro Glu
 30              35                  40                      45

AAT GGA GTG ACT TTA GCA CCA GAG GAT ACC TTG CCT TTC TTA AAG TGC       193
Asn Gly Val Thr Leu Ala Pro Glu Asp Thr Leu Pro Phe Leu Lys Cys
                 50                  55                  60

TAT TGC TCA GGA CAC TGC CCA GAT GAT GCT ATT AAT AAC ACA TGC ATA       241
Tyr Cys Ser Gly His Cys Pro Asp Asp Ala Ile Asn Asn Thr Cys Ile
                 65                  70                  75

ACT AAT GGC CAT TGC TTT GCC ATT ATA GAA GAA GAT GAT CAG GGA GAA       289
Thr Asn Gly His Cys Phe Ala Ile Ile Glu Glu Asp Asp Gln Gly Glu
         80                  85                  90

ACC ACA TTA ACT TCT GGG TGT ATG AAG TAT GAA GGC TCT GAT TTT CAA       337
Thr Thr Leu Thr Ser Gly Cys Met Lys Tyr Glu Gly Ser Asp Phe Gln
     95                 100                 105

TGC AAG GAT TCA CCG AAA GCC CAG CTA CGC AGG ACA ATA GAA TGT TGT       385
Cys Lys Asp Ser Pro Lys Ala Gln Leu Arg Arg Thr Ile Glu Cys Cys
110                 115                 120                 125

CGG ACC AAT TTG TGC AAC CAG TAT TTG CAG CCT ACA CTG CCC CCT GTT       433
Arg Thr Asn Leu Cys Asn Gln Tyr Leu Gln Pro Thr Leu Pro Pro Val
                130                 135                 140

GTT ATA GGT CCG TTC TTT GAT GGC AGC ATC CGA                           466
Val Ile Gly Pro Phe Phe Asp Gly Ser Ile Arg
                145                 150
```

(2) INFORMATION FOR SEQ ID NO: 6:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO: 6:

Met Thr Gln Leu Tyr Thr Tyr Ile Arg Leu Leu Gly Ala Cys Leu Phe
 1               5                  10                  15

Ile Ile Ser His Val Gln Gly Gln Asn Leu Asp Ser Met Leu His Gly
                20                  25                  30

Thr Gly Met Lys Ser Asp Leu Asp Gln Lys Lys Pro Glu Asn Gly Val
             35                  40                  45

Thr Leu Ala Pro Glu Asp Thr Leu Pro Phe Leu Lys Cys Tyr Cys Ser
 50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Thr Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Cys Arg Thr Asn
            115                 120                 125

Leu Cys Asn Gln Tyr Leu Gln Pro Thr Leu Pro Pro Val Val Ile Gly
130                 135                 140

Pro Phe Phe Asp Gly Ser Ile Arg
145                 150

(2) INFORMATION FOR SEQ ID NO: 7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 18..33
        (D) OTHER INFORMATION: /note= "n = inosine"

(xi) SEQUENCE DESCRIPTION: SEQ ID NO: 7:

GCGGAATTCT TRATRTCNCK RTGRCTNATN GCNGGYTT                                38

(2) INFORMATION FOR SEQ ID NO: 8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 18..33
        (D) OTHER INFORMATION: /note= "n = inosine"

(xi) SEQUENCE DESCRIPTION: SEQ ID NO: 8:

GCGGAATTCT TRATRTCNCK RTGNGMNATN GCNGGYTT                                38

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear

```
    (ix) FEATURE:
          (A) NAME/KEY: modified_base
          (B) LOCATION: 15..30
          (D) OTHER INFORMATION: /note= "n = inosine"

(xi) SEQUENCE DESCRIPTION: SEQ ID NO: 9:

ACTGAATTCG ARGCNGTNGC NGTNAARRTN TT                                    32

(2) INFORMATION FOR SEQ ID NO: 10:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ix) FEATURE:
          (A) NAME/KEY: modified_base
          (B) LOCATION: 18..30
          (D) OTHER INFORMATION: /note= "n = inosine"

(xi) SEQUENCE DESCRIPTION: SEQ ID NO: 10:

ACTGAATTCG ARTAYGTNGC NGTNAARRTN TT                                    32

(2) INFORMATION FOR SEQ ID NO: 11:

(i) SEQUENCE CHARACTERISTICS:
          (A) LENGTH: 378 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 11:
```

Gln Ile Arg Leu Thr Gly Arg Val Gly Ser Gly Arg Phe Gly Asn Val
 1               5                  10                  15

Ser Arg Gly Asp Tyr Arg Gly Glu Ala Val Ala Val Lys Val Phe Asn
             20                  25                  30

Ala Leu Asp Glu Pro Ala Phe His Lys Glu Thr Glu Ile Phe Glu Thr
         35                  40                  45

Arg Met Leu Arg His Pro Asn Val Leu Arg Tyr Ile Gly Ser Asp Arg
     50                  55                  60

Val Asp Thr Gly Phe Val Thr Glu Leu Trp Leu Val Thr Glu Tyr His
 65                  70                  75                  80

Pro Ser Gly Ser Leu His Asp Phe Leu Leu Glu Asn Thr Val Asn Ile
                 85                  90                  95

Glu Thr Tyr Tyr Asn Leu Met Arg Ser Thr Ala Ser Gly Leu Ala Phe
            100                 105                 110

Leu His Asn Gln Ile Gly Gly Ser Lys Glu Ser Asn Lys Pro Ala Met
        115                 120                 125

Ala His Arg Asp Ile Lys Ser Lys Asn Ile Met Val Lys Asn Asp Leu
    130                 135                 140

Thr Cys Ala Ile Gly Asp Leu Gly Leu Ser Leu Ser Lys Pro Glu Asp
145                 150                 155                 160

Ala Ala Ser Asp Ile Ile Ala Asn Glu Asn Tyr Lys Cys Gly Thr Val
                165                 170                 175

Arg Tyr Leu Ala Pro Glu Ile Leu Asn Ser Thr Met Gln Phe Thr Val
            180                 185                 190

Phe Glu Ser Tyr Gln Cys Ala Asp Val Tyr Ser Phe Ser Leu Val Met
        195                 200                 205

```
Trp Glu Thr Leu Cys Arg Cys Glu Asp Gly Asp Val Leu Pro Arg Glu
210                 215                 220

Ala Ala Thr Val Ile Pro Tyr Ile Glu Trp Thr Asp Arg Asp Pro Gln
225                 230                 235                 240

Asp Ala Gln Met Phe Asp Val Val Cys Thr Arg Arg Leu Arg Pro Thr
                245                 250                 255

Glu Asn Pro Leu Trp Lys Asp His Pro Glu Met Lys His Ile Met Glu
            260                 265                 270

Ile Ile Lys Thr Cys Trp Asn Gly Asn Pro Ser Ala Arg Phe Thr Ser
            275                 280                 285

Tyr Ile Cys Arg Lys Arg Met Asp Glu Arg Gln Gln Leu Leu Leu Asp
        290                 295                 300

Lys Lys Ala Lys Ala Val Ala Gln Thr Ala Gly Val Thr Val Gln Asp
305                 310                 315                 320

Arg Lys Ile Leu Gly Pro Gln Lys Pro Lys Asp Glu Ser Pro Ala Asn
                325                 330                 335

Gly Ala Pro Arg Ile Val Gln Lys Glu Ile Asp Arg Glu Asp Glu Gln
                340                 345                 350

Glu Asn Trp Arg Glu Thr Ala Lys Thr Pro Asn Gly His Ile Ser Ser
            355                 360                 365

Asn Asp Asp Ser Ser Arg Pro Leu Leu Gly
370                 375

(2) INFORMATION FOR SEQ ID NO: 12:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Pro Leu Gln Leu Leu Glu Val Lys Ala Arg Gly Arg Phe Gly Cys Val
1               5                   10                  15

Trp Lys Ala Gln Leu Leu Asn Glu Tyr Val Ala Val Lys Ile Phe Pro
                20                  25                  30

Ile Gln Asp Lys Gln Ser Trp Gln Asn Glu Tyr Glu Val Tyr Ser Leu
            35                  40                  45

Pro Gly Met Lys His Glu Asn Ile Leu Gln Phe Ile Gly Ala Glu Lys
        50                  55                  60

Arg Gly Thr Ser Val Asp Val Asp Leu Trp Leu Ile Thr Ala Phe His
65                  70                  75                  80

Glu Lys Gly Ser Leu Ser Asp Phe Leu Lys Ala Asn Val Val Ser Trp
                85                  90                  95

Asn Glu Leu Cys His Ile Ala Glu Thr Met Ala Arg Gly Leu Ala Tyr
            100                 105                 110

Leu His Glu Asp Ile Pro Gly Leu Lys Asp Gly His Lys Pro Ala Ile
        115                 120                 125

Ser His Arg Asp Ile Lys Ser Lys Asn Val Leu Leu Lys Asn Asn Leu
    130                 135                 140

Thr Ala Cys Ile Ala Asp Phe Gly Leu Ala Leu Lys Phe Glu Ala Gly
145                 150                 155                 160

Lys Ser Ala Gly Asp Thr His Gly Gln Val Gly Thr Arg Arg Tyr Met
                165                 170                 175
```

```
Ala Pro Glu Val Leu Glu Gly Ala Ile Asn Phe Gln Arg Asp Ala Phe
            180                 185                 190

Leu Arg Ile Asp Met Tyr Ala Met Gly Leu Val Leu Trp Glu Leu Ala
            195                 200                 205

Ser Arg Cys Thr Ala Ala Asp Gly Pro Val Asp Glu Tyr Met Leu Pro
            210                 215                 220

Phe Glu Glu Glu Ile Gly Gln His Pro Ser Leu Glu Asp Met Gln Glu
225                 230                 235                 240

Val Val Val His Lys Lys Arg Pro Val Leu Arg Asp Tyr Trp Gln
                245                 250                 255

Lys His Ala Gly Met Ala Met Leu Cys Glu Thr Ile Glu Glu Cys Trp
            260                 265                 270

Asp His Asp Ala Glu Ala Arg Leu Ser Ala Gly Cys Val Gly Glu Arg
            275                 280                 285

Ile Thr Gln Met Gln Arg Leu Thr Asn Ile Ile Thr Thr Glu Asp Ile
            290                 295                 300

Val Thr Val Val Thr Met Val Thr Asn Val Asp Phe Pro Pro Lys Glu
305                 310                 315                 320

Ser Ser Leu (2) INFORMATION FOR SEQ ID NO: 13:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Pro Ile Glu Leu Asp Thr Leu Val Gly Lys Gly Arg Phe Ala Glu Val
1               5                   10                  15

Tyr Lys Ala Lys Leu Lys Gln Asn Thr Ser Glu Gln Phe Glu Thr Val
            20                  25                  30

Ala Val Lys Ile Phe Pro Tyr Glu Glu Tyr Ser Ser Trp Lys Thr Glu
            35                  40                  45

Lys Asp Ile Phe Ser Asp Ile Asn Leu Lys His Glu Asn Ile Leu Gln
50                  55                  60

Phe Leu Thr Ala Glu Glu Arg Lys Thr Glu Met Gly Lys Gln Tyr Trp
65                  70                  75                  80

Leu Ile Thr Ala Phe His Ala Lys Gly Asn Leu Gln Glu Tyr Leu Thr
            85                  90                  95

Arg His Val Ile Ser Trp Glu Asp Leu Arg Lys Leu Gly Ser Ser Leu
            100                 105                 110

Ala Arg Gly Ile Ala His Leu His Ser Asp His Thr Pro Cys Gly Arg
            115                 120                 125

Pro Lys Met Pro Ile Val His Arg Asp Leu Lys Ser Ser Asn Ile Leu
            130                 135                 140

Val Lys Asn Asp Leu Thr Cys Cys Leu Cys Asp Phe Gly Leu Ser Leu
145                 150                 155                 160

Arg Leu Asp Pro Thr Leu Ser Val Asp Asp Leu Ala Asn Ser Gly Gln
            165                 170                 175

Val Gly Thr Ala Arg Tyr Met Ala Pro Glu Val Leu Glu Ser Arg Met
            180                 185                 190

Asn Leu Glu Asn Met Glu Ser Phe Lys Gln Thr Asp Val Tyr Ser Met
```

-continued

```
            195                 200                 205
Ala Leu Val Leu Trp Glu Met Thr Ser Arg Cys Asn Ala Val Gly Glu
        210                 215                 220

Val Lys Asp Tyr Glu Pro Pro Phe Gly Ser Lys Val Arg Glu His Pro
225                 230                 235                 240

Cys Val Glu Ser Met Lys Asp Asn Val Leu Arg Asp Arg Gly Arg Pro
                245                 250                 255

Glu Ile Pro Ser Phe Trp Leu Asn His Gln Gly Ile Gln Ile Val Cys
            260                 265                 270

Glu Thr Leu Thr Glu Cys Trp Asp His Asp Pro Glu Ala Arg Leu Thr
        275                 280                 285

Ala Gln Cys Val Ala Glu Arg Phe Ser Glu Leu Glu His Pro Asp Arg
    290                 295                 300

Leu Ser Gly Arg Ser Cys Ser Gln Glu Lys Ile Pro Glu Asp Gly Ser
305                 310                 315                 320

Leu Asn Thr Thr Lys
                325
```

(2) INFORMATION FOR SEQ ID NO: 14:

(i) SEQUENCE CHARACTERISTICS:
      (A) LENGTH: 303 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 14:

```
Gln Ile Thr Leu Leu Glu Cys Val Gly Lys Gly Arg Tyr Gly Glu Val
1               5                   10                  15

Trp Arg Gly Ser Trp Gln Gly Glu Asn Val Ala Val Lys Ile Phe Ser
            20                  25                  30

Ser Arg Asp Glu Lys Ser Trp Phe Arg Glu Thr Glu Leu Tyr Asn Thr
        35                  40                  45

Val Met Leu Arg His Glu Asn Ile Leu Gly Phe Ile Ala Ser Asp Met
    50                  55                  60

Thr Ser Arg His Ser Ser Thr Gln Leu Trp Leu Ile Thr His Tyr His
65                  70                  75                  80

Glu Met Gly Ser Leu Tyr Asp Tyr Leu Gln Leu Thr Thr Leu Asp Thr
                85                  90                  95

Val Ser Cys Leu Arg Ile Val Leu Ser Ile Ala Ser Gly Leu Ala His
            100                 105                 110

Leu His Ile Glu Ile Phe Gly Thr Gln Gly Lys Ser Ala Ile Ala His
        115                 120                 125

Arg Asp Leu Lys Ser Lys Asn Ile Leu Val Lys Lys Asn Gly Gln Cys
    130                 135                 140

Cys Ile Ala Asp Leu Gly Leu Ala Val Met His Ser Gln Ser Thr Asn
145                 150                 155                 160

Gln Leu Asp Val Gly Asn Asn Pro Arg Val Gly Thr Lys Arg Tyr Met
                165                 170                 175

Ala Pro Glu Val Leu Asp Glu Thr Ile Gln Val Asp Cys Phe Asp Ser
            180                 185                 190

Tyr Lys Arg Val Asp Ile Trp Ala Phe Gly Leu Val Leu Trp Glu Val
        195                 200                 205

Ala Arg Arg Met Val Ser Asn Gly Ile Val Glu Asp Tyr Lys Pro Pro
```

```
                     210                 215                 220
Phe Tyr Asp Val Val Pro Asn Asp Pro Ser Phe Glu Asp Met Arg Lys
225                 230                 235                 240

Val Val Cys Val Asp Gln Gln Arg Pro Asn Ile Pro Asn Arg Trp Phe
                245                 250                 255

Ser Asp Pro Thr Leu Thr Ser Leu Ala Lys Leu Met Lys Glu Cys Trp
            260                 265                 270

Tyr Gln Asn Pro Ser Ala Arg Leu Thr Ala Leu Arg Ile Lys Lys Thr
        275                 280                 285

Leu Thr Lys Ile Asp Asn Ser Leu Asp Lys Leu Lys Thr Asp Cys
    290                 295                 300

(2) INFORMATION FOR SEQ ID NO: 15:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Gln Val Ala Leu Val Glu Cys Val Gly Lys Gly Arg Tyr Gly Glu Val
1               5                   10                  15

Trp Arg Gly Ser Trp His Gly Glu Ser Val Ala Val Lys Ile Phe Ser
            20                  25                  30

Ser Arg Asp Glu Gln Ser Trp Phe Arg Glu Thr Glu Ile Tyr Asn Thr
        35                  40                  45

Val Leu Leu Arg His Asp Asn Ile Leu Gly Phe Ile Ala Ser Asp Met
    50                  55                  60

Thr Ser Arg Asn Ser Ser Thr Gln Leu Trp Leu Ile Thr His Tyr His
65                  70                  75                  80

Glu His Gly Ser Leu Tyr Asp Phe Leu Gln Arg Gln Thr Leu Glu Pro
                85                  90                  95

Gln Leu Ala Leu Arg Leu Ala Val Ser Ala Ala Cys Gly Leu Ala His
            100                 105                 110

Leu His Val Glu Ile Phe Gly Thr Gln Gly Lys Pro Ala Ile Ala His
        115                 120                 125

Arg Asp Leu Lys Ser Arg Asn Val Leu Val Lys Ser Asn Leu Gln Cys
    130                 135                 140

Cys Ile Ala Asp Leu Gly Leu Ala Val Met His Ser Gln Ser Ser Asp
145                 150                 155                 160

Tyr Leu Asp Ile Gly Asn Asn Pro Arg Val Gly Thr Lys Arg Tyr Met
                165                 170                 175

Ala Pro Glu Val Leu Asp Glu Gln Ile Arg Thr Asp Cys Phe Glu Ser
            180                 185                 190

Tyr Lys Trp Thr Asp Ile Trp Ala Phe Gly Leu Val Leu Trp Glu Ile
        195                 200                 205

Ala Arg Arg Thr Ile Ile Asn Gly Ile Val Glu Asp Tyr Arg Pro Pro
    210                 215                 220

Phe Tyr Asp Met Val Pro Asn Asp Pro Ser Phe Glu Asp Met Lys Lys
225                 230                 235                 240

Val Val Cys Val Asp Gln Gln Thr Pro Thr Ile Pro Asn Arg Leu Ala
                245                 250                 255

Ala Asp Pro Val Leu Ser Gly Leu Ala Gln Met Met Arg Glu Cys Trp
```

```
                    260                 265                 270
Tyr Pro Asn Pro Ser Ala Arg Leu Thr Ala Leu Arg Ile Lys Lys Thr
                275                 280                 285

Leu Gln Lys Leu Ser Gln Asn Pro Glu Lys Pro Lys Val Ile His
            290                 295                 300
```

(2) INFORMATION FOR SEQ ID NO: 16:

(i) SEQUENCE CHARACTERISTICS:
       (A) LENGTH: 300 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 16:

```
Thr Ile Val Leu Gln Glu Ile Gly Lys Gly Arg Phe Gly Glu Val
1               5                  10                  15

Trp Arg Gly Arg Trp Arg Gly Gly Asp Val Ala Val Lys Ile Phe Ser
                20                  25                  30

Ser Arg Glu Glu Arg Ser Trp Phe Arg Glu Ala Glu Ile Tyr Gln Thr
                35                  40                  45

Val Met Leu Arg His Glu Asn Ile Leu Gly Phe Ile Ala Ala Asp Asn
            50                  55                  60

Lys Asp Asn Gly Thr Trp Thr Gln Leu Trp Leu Val Ser Asp Tyr His
65                  70                  75                  80

Glu His Gly Ser Leu Phe Asp Tyr Leu Asn Arg Tyr Thr Val Thr Ile
                    85                  90                  95

Glu Gly Met Ile Lys Leu Ala Leu Ser Ala Ala Ser Gly Leu Ala His
                100                 105                 110

Leu His Met Glu Ile Val Gly Thr Gln Gly Lys Pro Gly Ile Ala His
            115                 120                 125

Arg Asp Leu Lys Ser Lys Asn Ile Leu Val Lys Lys Asn Gly Met Cys
        130                 135                 140

Ala Ile Ala Asp Leu Gly Leu Ala Val Arg His Asp Ala Val Thr Asp
145                 150                 155                 160

Thr Ile Asp Ile Ala Pro Asn Gln Arg Val Gly Thr Lys Arg Tyr Met
                165                 170                 175

Ala Pro Glu Val Leu Asp Glu Thr Ile Asn Met Lys His Phe Asp Ser
            180                 185                 190

Phe Lys Cys Ala Asp Ile Tyr Ala Leu Gly Leu Val Tyr Trp Glu Ile
        195                 200                 205

Ala Arg Arg Cys Asn Ser Gly Gly Val His Glu Glu Tyr Gln Leu Pro
    210                 215                 220

Tyr Tyr Asp Leu Val Pro Ser Asp Pro Ser Ile Glu Glu Met Arg Lys
225                 230                 235                 240

Val Val Cys Asp Gln Lys Leu Arg Pro Asn Val Pro Asn Trp Trp Gln
                245                 250                 255

Ser Tyr Glu Ala Leu Arg Val Met Gly Lys Met Met Arg Glu Cys Trp
            260                 265                 270

Tyr Ala Asn Gly Ala Ala Arg Leu Thr Ala Leu Arg Ile Lys Lys Thr
        275                 280                 285

Leu Ser Gln Leu Ser Val Gln Glu Asp Val Lys Ile
    290                 295                 300
```

(2) INFORMATION FOR SEQ ID NO: 17:

(i) SEQUENCE CHARACTERISTICS:
        (A) LENGTH: 300 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Thr Ile Val Leu Gln Glu Ser Ile Gly Lys Gly Arg Phe Gly Glu Val
  1               5                  10                  15

Trp Arg Gly Lys Trp Arg Gly Glu Glu Val Ala Val Lys Ile Phe Ser
             20                  25                  30

Ser Arg Glu Glu Arg Ser Trp Phe Arg Glu Ala Glu Ile Tyr Gln Thr
         35                  40                  45

Val Met Leu Arg His Glu Asn Ile Leu Gly Phe Ile Ala Ala Asp Asn
 50                  55                  60

Lys Asp Asn Gly Thr Trp Thr Gln Leu Trp Leu Val Ser Asp Tyr His
 65                  70                  75                  80

Glu His Gly Ser Leu Phe Asp Tyr Leu Asn Arg Tyr Thr Val Thr Val
                 85                  90                  95

Glu Gly Met Ile Lys Leu Ala Leu Ser Thr Ala Ser Gly Leu Ala His
                100                 105                 110

Leu His Met Glu Ile Val Gly Thr Gln Gly Lys Pro Ala Ile Ala His
            115                 120                 125

Arg Asp Leu Lys Ser Lys Asn Ile Leu Val Lys Lys Asn Gly Thr Cys
130                 135                 140

Cys Ile Ala Asp Leu Gly Leu Ala Val Arg His Asp Ser Ala Thr Asp
145                 150                 155                 160

Thr Ile Asp Ile Ala Pro Asn His Arg Val Gly Thr Lys Arg Tyr Met
                165                 170                 175

Ala Pro Glu Val Leu Asp Asp Ser Ile Asn Met Lys His Phe Glu Ser
            180                 185                 190

Phe Lys Arg Ala Asp Ile Tyr Ala Met Gly Leu Val Phe Trp Glu Ile
        195                 200                 205

Ala Arg Arg Cys Ser Ile Gly Gly Ile His Glu Asp Tyr Gln Leu Pro
    210                 215                 220

Tyr Tyr Asp Leu Val Pro Ser Asp Pro Ser Val Glu Glu Met Arg Lys
225                 230                 235                 240

Val Val Cys Glu Gln Lys Leu Arg Pro Asn Ile Pro Asn Arg Trp Gln
                245                 250                 255

Ser Cys Glu Ala Leu Arg Val Met Ala Lys Ile Met Arg Glu Cys Trp
            260                 265                 270

Tyr Ala Asn Gly Ala Ala Arg Leu Thr Ala Leu Arg Ile Lys Lys Thr
        275                 280                 285

Leu Ser Gln Leu Ser Gln Gln Glu Gly Ile Lys Met
290                 295                 300
```

(2) INFORMATION FOR SEQ ID NO: 18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:

(A) NAME/KEY: Peptide
            (B) LOCATION: 2
            (D) OTHER INFORMATION: /product= "OTHER"
                /note= "May also be Tyr"

(ix) FEATURE:
            (A) NAME/KEY: Peptide
            (B) LOCATION: 7
            (D) OTHER INFORMATION: /product= "OTHER"
                /note= "May also be Ile"

(xi) SEQUENCE DESCRIPTION: SEQ ID NO: 18:

Glu Ala Val Ala Val Lys Val Phe
1               5

(2) INFORMATION FOR SEQ ID NO: 19:

(i) SEQUENCE CHARACTERISTICS:
            (A) LENGTH: 10 amino acids
            (B) TYPE: amino acid
            (C) STRANDEDNESS: single
            (D) TOPOLOGY: linear (ix) FEATURE:
            (A) NAME/KEY: Peptide
            (B) LOCATION: 4
            (D) OTHER INFORMATION: /product= "OTHER"
                /note= "May also be Ile"

(ix) FEATURE:
            (A) NAME/KEY: Peptide
            (B) LOCATION: 5
            (D) OTHER INFORMATION: /product= "OTHER"
                /note= "May also be Ser"

(xi) SEQUENCE DESCRIPTION: SEQ ID NO: 19:

Lys Pro Ala Met Ala His Arg Asp Ile Lys
1               5                   10

(2) INFORMATION FOR SEQ ID NO: 20:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 20:

CCATAGATCT CAGAATCTAG ATAGT                                           25

(2) INFORMATION FOR SEQ ID NO: 21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 21:

GGTAAGATCT TCGGATCCTG CCATC                                           25

(2) INFORMATION FOR SEQ ID NO: 22:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide -continued (xi) SEQUENCE DESCRIPTION: SEQ ID NO: 22:

```
Leu Asn Thr Arg Val Gly Thr Lys Arg Tyr Met Ala Pro Glu Val Leu
1               5                   10                  15
Asp Glu Ser Leu Asn Lys Asn Cys
            20
```